(12) United States Patent
Avinash et al.

(10) Patent No.: US 8,180,125 B2
(45) Date of Patent: May 15, 2012

(54) MEDICAL DATA PROCESSING AND VISUALIZATION TECHNIQUE

(75) Inventors: Gopal B. Avinash, Menomonee Falls, WI (US); Saad Ahmed Sirohey, Pewaukee, WI (US); Fausto J. Espinal, Waukesha, WI (US); Zhongmin Lin, New Berlin, WI (US); Ananth Mohan, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1030 days.

(21) Appl. No.: 12/123,911

(22) Filed: May 20, 2008

(65) Prior Publication Data

US 2009/0290772 A1 Nov. 26, 2009

(51) Int. Cl.
*G06K 9/18* (2006.01)
*G06Q 50/00* (2006.01)

(52) U.S. Cl. ............................................ 382/128; 705/3

(58) Field of Classification Search .................. None
See application file for complete search history.

(56) References Cited

U.S. PATENT DOCUMENTS

| | | | |
|---|---|---|---|
| 8,010,381 B2 * | 8/2011 | Sirohey et al. ..................... 705/2 |
| 2007/0003117 A1 * | 1/2007 | Wheeler et al. ............... 382/128 |
| 2007/0078873 A1 | 4/2007 | Avinash et al. |
| 2007/0081699 A1 | 4/2007 | Avinash et al. |
| 2007/0081700 A1 | 4/2007 | Blumefeld et al. |
| 2007/0081701 A1 | 4/2007 | Sirohey et al. |
| 2007/0081707 A1 | 4/2007 | Sirohey et al. |
| 2008/0126118 A1 | 5/2008 | Sirohey et al. |
| 2008/0126119 A1 | 5/2008 | Sirohey et al. |
| 2008/0126120 A1 | 5/2008 | Sirohey et al. |
| 2008/0126121 A1 | 5/2008 | Sirohey et al. |
| 2009/0138279 A1 | 5/2009 | Avinash et al. |
| 2009/0292478 A1 | 11/2009 | Avinash et al. |
| 2009/0292551 A1 | 11/2009 | Sirohey et al. |
| 2009/0292557 A1 | 11/2009 | Sirohey et al. |

FOREIGN PATENT DOCUMENTS

JP 2006204641 8/2006

OTHER PUBLICATIONS

Minoshima et al., "A Diagnostic Approach in Alzheimer's Disease Using Three-Dimensional Stereotactic Surface Projections of Fluorine-18-FDG PET", The Journal of Nuclear Medicine, Jul. 1995, pp. 1238-1248, vol. 36, No. 7.

Dale et al., "Cortical Surface-Based Analysis, I. Segmentation and Surface Reconstruction," NeuroImage 9, 1999, pp. 179-194, Academic Press.

Hutton et al, "Sulcal Segmentation for Cortical Thickness Measurements," MICCAI, 2002, pp. 443-450, Springer-Verlag, Berlin, Heidelberg.

(Continued)

*Primary Examiner* — Roberto Velez
(74) *Attorney, Agent, or Firm* — Fletcher Yoder, P.C.

(57) ABSTRACT

A data processing technique is provided. In one embodiment, a computer-implemented method includes accessing patient image and non-image deviation scores derived through respective comparisons of patient image and non-image data to standardized image and non-image data. The method may also include processing the image and non-image deviation scores to generate a visual output indicative of differences between the patient image and non-image data, and the standardized image and non-image data, respectively. Further, the method may include displaying the visual output. Additional methods, systems, and manufactures are also disclosed.

13 Claims, 21 Drawing Sheets

OTHER PUBLICATIONS

Scott et al., "Cerebral Cortical Thickness Measurements," University of Manchester, Imaging Science and Biomedical Engineering Division, Medical School, Feb. 15, 2005, pp. 1-25, Manchester.

GE Healthcare Cortex ID User Guide, Revision 2, 2006, pp. ii-39.

Mosconi et al., "Multicenter Standardized 18F-FDG PET Diagnosis of Mild Cognitive Impairment, Alzheimer's Disease, and Other Dementias", Mar. 2008, pp. 390-397, vol. 49, No. 3, Revision 2, The Journal of Nuclear Medicine.

* cited by examiner

MEDICAL DATA PROCESSING AND VISUALIZATION TECHNIQUE

BACKGROUND

The present invention relates generally to medical diagnosis and, more particularly, to the diagnosis of medical conditions from patient deviation data.

One type of medical condition or disease that is of interest to the medical community is neurodegenerative disorders (NDDs), such as Alzheimer's disease and Parkinson's disease. Alzheimer's disease currently afflicts tens of millions of people worldwide, and accounts for a majority of dementia cases in patients. Further, there is not, as of yet, any known cure. The economic and social costs associated with Alzheimer's disease are significant, and are increasing over time.

However, NDDs may be challenging to treat and/or study because they are both difficult to detect at an early stage, and hard to quantify in a standardized manner for comparison across different patient populations. In response to these difficulties, investigators have developed methods to determine statistical deviations from normal patient populations. One element of the detection of NDD is the development of age and tracer segregated normal databases. Comparison to these normals can only happen in a standardized domain, e.g., the Talairach domain or the Montreal Neurological Institute (MNI) domain. The MNI defines a standard brain by using a large series of magnetic resonance imaging (MRI) scans on normal controls. The Talairach domain references a brain that is dissected and photographed for the Talairach and Toumoux atlases. In both the Talairach domain and the MNI domain, data must be mapped to the respective standard domain using registration techniques. Current methods that use a variation of the above method include tracers NeuroQ®, Statistical Parametric matching (SPM), 3D-sterotactic surface projections (3D-SSP), and so forth.

Once a comparison has been made, an image representing a statistical deviation of the anatomy is displayed, allowing a viewer to make a diagnosis based on the image. Making such a diagnosis is a very specialized task and is typically performed by highly-trained medical image experts. However, even such experts can only make a subjective call as to the degree of severity of the disease. Due to this inherent subjectivity, the diagnoses tend to be inconsistent and non-standardized. It may, therefore, be desirable to increase the consistency and standardization of such diagnoses. It may also be desirable to incorporate additional data, including non-image data, to provide a holistic approach to patient diagnosis.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

According to one embodiment, a system includes a memory device having a plurality of routines stored therein, and a processor configured to execute the plurality of routines stored in the memory device. The plurality of routines may include a routine configured to effect accessing of a patient image deviation score indicative of a difference between patient image data and reference image data representative of a population segment. Further, the plurality of routines may include a routine configured to effect accessing of a patient non-image deviation score indicative of a difference between patient non-image data and reference non-image data representative of the population segment. Additionally, the plurality of routines may further include routines configured to effect generating of a report having visual indications of deviations of the patient image and non-image data from the respective reference image and non-image data, and to effect outputting of the report.

According to another embodiment, a computer-implemented method includes accessing at least one patient image deviation score derived through a comparison of patient image data to standardized image data representative of a population of individuals. The method may also include accessing one or more patient non-image deviation scores derived through a comparison of patient non-image data to standardized non-image data representative of the population of individuals. Still further, the method may include processing the image and non-image deviation scores to generate a visual output indicative of differences between the patient data and the standardized data, and may include displaying the visual output to facilitate diagnosis of a patient medical condition.

According to a further embodiment, a computer-implemented method includes accessing an image deviation score of a patient calculated from a comparison of patient image data from at least two different imaging modalities to standardized image data. The method may also include processing the image deviation score to generate a visual output including a graphical representation indicative of a difference between the patient image data and the standardized image data. Still further, the method may include displaying the visual output.

According to yet another embodiment, a computer-implemented method includes accessing patient non-image deviation scores calculated from a comparison of longitudinal patient non-image data with standardized non-image data. The method may also include processing the patient non-image deviation scores to generate a visual output including a graphical representation indicative of a difference between at least a subset of the longitudinal patient non-image data and the standardized non-image data. Still further, the method may include displaying the visual output.

According to yet another embodiment, a manufacture includes a computer-readable medium having executable instructions stored thereon. The executable instructions may include instructions adapted to access a patient image deviation score derived from a comparison of patient image data to reference image data. The executable instructions may also include instructions adapted to access a patient non-image deviation score derived through a comparison of patient non-image data to reference non-image data. Further, the executable instructions may include instructions adapted to generate, based at least in part on the image and non-image deviation scores, and to display a visual output indicative of a difference between the patient image data and the reference image data, and of a difference between the patient non-image data and the reference non-image data.

Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

Figure 21:
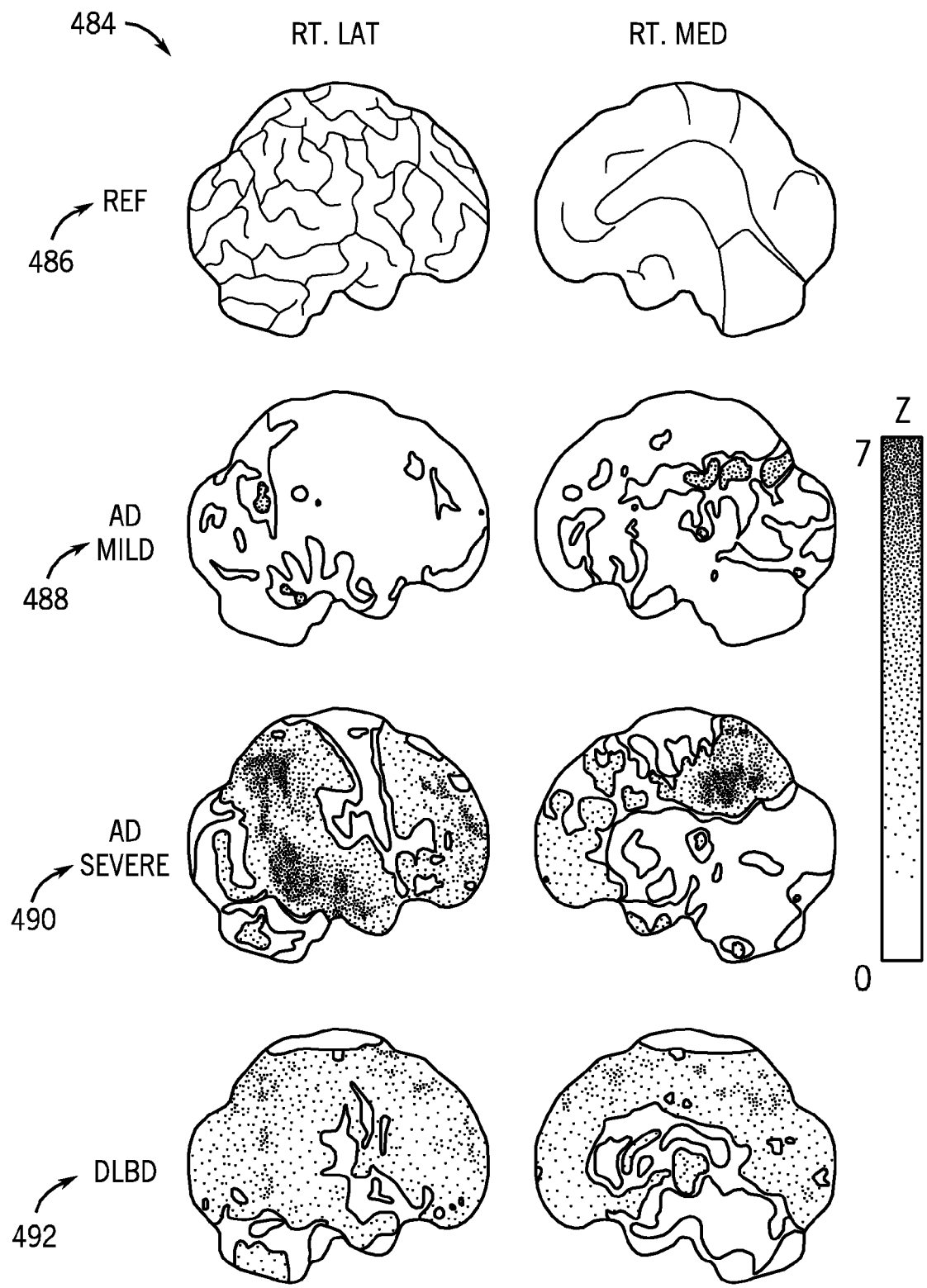
Figure 22:
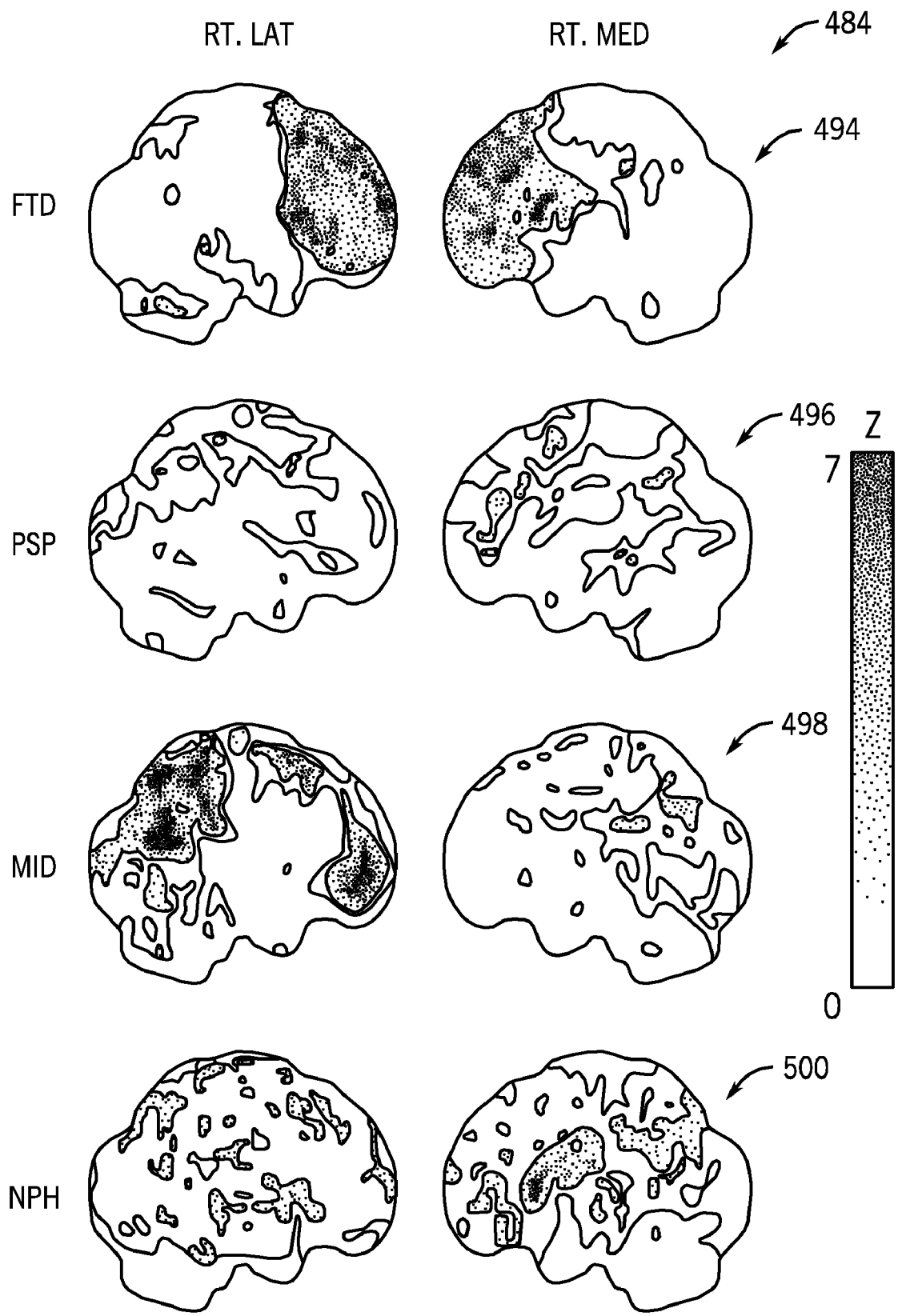

FIG. 21 illustrates a plurality of representative reference deviation maps that may be contained in a reference library or database of such deviation maps in accordance with one embodiment of the present invention; and FIG. 22 illustrates additional representative reference deviation maps that may be contained in a reference library or database of deviation maps in accordance with one embodiment of the present invention.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
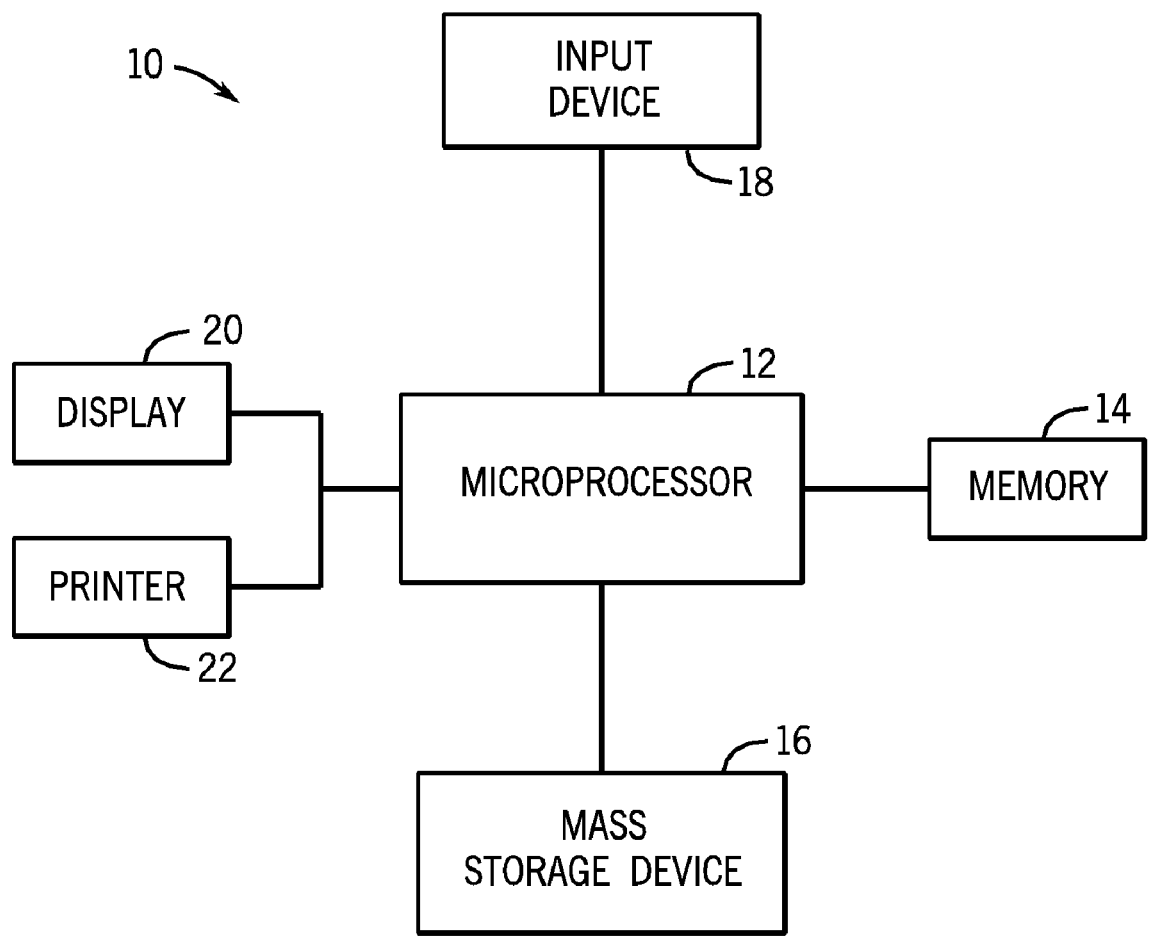
FIG. 1 is a block diagram of an exemplary processor-based device or system in accordance with one embodiment of the present invention.

Turning now to the drawings, and referring first to FIG. 1, an exemplary processor-based system 10 for use in conjunction with the present technique is depicted. In one embodiment, the exemplary processor-based system 10 is a general-purpose computer, such as a personal computer, configured to run a variety of software, including software implementing all or part of the presently disclosed techniques, including the methods and functionality described throughout the instant disclosure. Alternatively, in other embodiments, the processor-based system 10 may comprise, among other things, a mainframe computer, a distributed computing system, or an application-specific computer or workstation configured to implement all or part of the present techniques based on specialized software and/or hardware provided as part of the system. Further, the processor-based system 10 may include either a single processor or a plurality of processors to facilitate implementation of the presently disclosed functionality.

In general, the exemplary processor-based system 10 includes a microcontroller or microprocessor 12, such as a central processing unit (CPU), which executes various routines and processing functions of the system 10. For example, the microprocessor 12 may execute various operating system instructions as well as software routines configured to effect certain processes stored in or provided by a manufacture including a computer readable-medium, such as a memory 14 (e.g., a random access memory (RAM) of a personal computer) or one or more mass storage devices 16 (e.g., an internal or external hard drive, a solid-state storage device, CD-ROM, DVD, or other storage device). In addition, the microprocessor 12 processes data provided as inputs for various routines or software programs, such as data provided in conjunction with the present techniques in computer-based implementations.

Such data may be stored in, or provided by, the memory 14 or mass storage device 16. Alternatively, such data may be provided to the microprocessor 12 via one or more input devices 18. As will be appreciated by those of ordinary skill in the art, the input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network, such as a local area network or the Internet. Through such a network device, the system 10 may exchange data and communicate with other networked electronic systems, whether proximate to or remote from the system 10. It will be appreciated that the network may include various components that facilitate communication, including switches, routers, servers or other computers, network adapters, communications cables, and so forth.

Results generated by the microprocessor 12, such as the results obtained by processing data in accordance with one or more stored routines, may be stored in a memory device, may undergo additional processing, or may be provided to an operator via one or more output devices, such as a display 20 and/or a printer 22. Also, based on the displayed or printed output, an operator may request additional or alternative processing or provide additional or alternative data, such as via the input device 18. As will be appreciated by those of ordinary skill in the art, communication between the various components of the processor-based system 10 may typically be accomplished via a chipset and one or more busses or interconnects which electrically connect the components of the system 10. Notably, in certain embodiments of the present techniques, the exemplary processor-based system 10 may be configured to facilitate patient diagnosis, as discussed in greater detail below.

Figure 2:
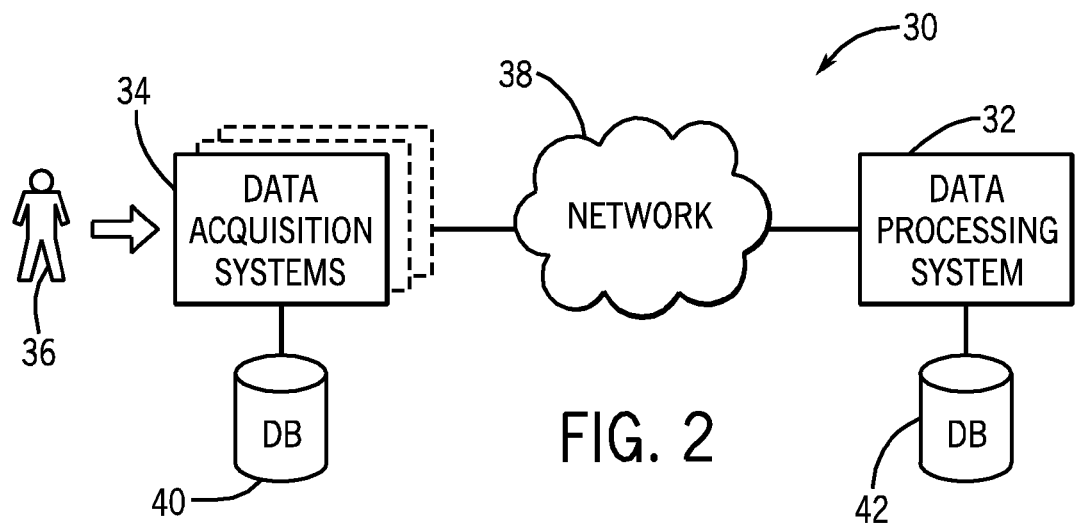
FIG. 2 is a block diagram of an exemplary data acquisition and processing system in accordance with one embodiment of the present invention.

An exemplary system 30 for acquiring and processing data is illustrated in FIG. 2 in accordance with one embodiment of the present invention. The system 30 includes a data processing system 32 configured to provide various functionality. It should be noted that, in one embodiment, the data processing system 32 may include a processor-based system, such as system 10, having any suitable combination of hardware and/or software code, routines, modules, or instructions adapted to perform the presently discussed functionality, including performance of various steps of the methods described elsewhere herein. It should be noted that such software routines may be embodied in a manufacture (e.g., a compact disc, a hard drive, a flash memory, RAM, or the like) and configured to be executed by a processor to effect performance of the functionality described herein.

The system 30 may also include one or more data acquisition systems 34 for collecting data from, or regarding, a patient 36. The patient data may include one or both of image data and non-image data, and may include any of static data, dynamic data, and longitudinal data. In various embodiments, the data acquisition systems 34 may include patient monitors, imaging systems of various modalities, computers, or any other suitable systems capable of collecting or receiving data regarding the patient 36. For instance, the data acquisition systems 34 may include, among others, an X-ray system, a computed tomography (CT) imaging system, a magnetic resonance (MR) imaging system, a positron emission tomography (PET) imaging system, a single photon emission computed tomography (SPECT) imaging system, a digital tomosynthesis imaging system, an electroencephalography (EEG) system, an electrocardiography (ECG or EKG) system, an electromyography (EMG) system, an electrical impedance tomography (EIT) system, an electronystagmography (ENG) system, a system adapted to collect nerve conduction data, or some combination of these systems.

Various components of the system 30, including the data processing system 32 and the data acquisition systems 34, may be connected to one another via a network 38 that facilitates communication between such components. The system 30 may also include one or more databases, such as databases 40 and 42, for storing data, such as data collected by the data acquisition systems 34 and data used by or generated from the data processing system 32, including both patient data and standardized reference data, as discussed in greater detail below. Additionally, the data processing system 32 may receive data directly from the data acquisition systems 32, from the databases 40 and 42, or in any other suitable fashion.

Figure 3:
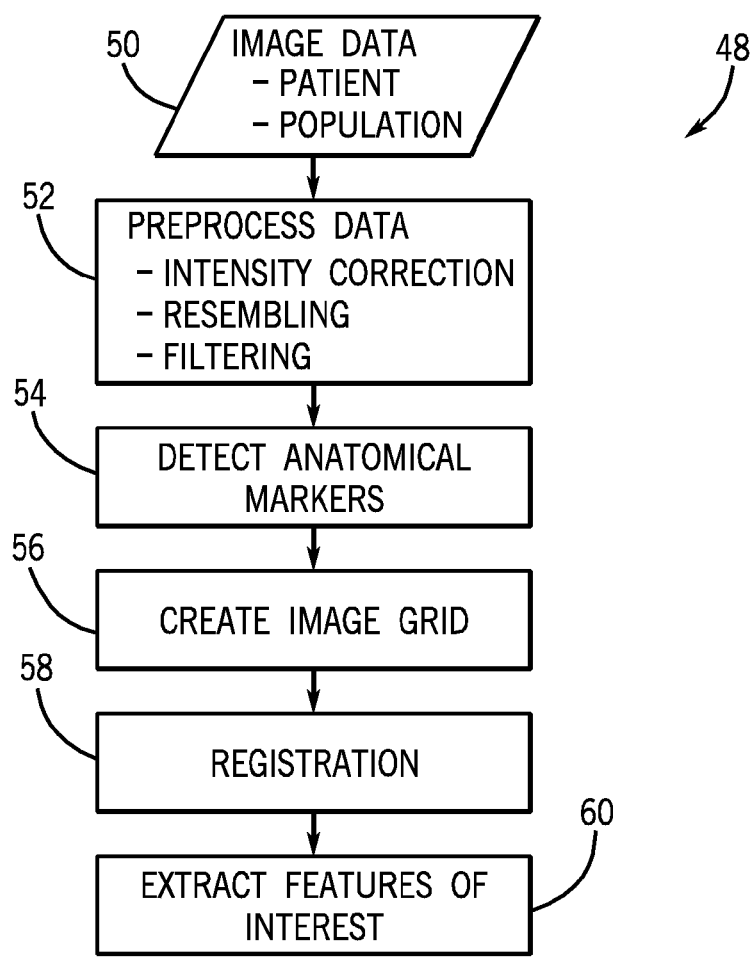
FIG. 3 is a flow chart of an exemplary method for preparing image data for feature extraction in accordance with one embodiment of the present invention.

In some embodiments, it may be desirable to analyze one or more features of interest from image data to facilitate diagnosis of a patient with respect to one or more disease types or disease severity levels. Accordingly, an exemplary method 48 for preparing image data for feature extraction is generally illustrated in FIG. 3 in accordance with one embodiment of the present invention. Image data 50 may be obtained from various sources, such as one or more of the data acquisition systems 34, the databases 40 or 42, or the like. Further, such image data may be related to a particular patient, such as the patient 36, or to one or more reference individuals of population sample. The method 48 may include various steps, such as steps 52, 54, 56, 58, and 60, for processing, registering, and extracting features of interest.

In the presently illustrated embodiment, the method 48 includes a step 52 of preprocessing the image data. Such preprocessing may include a host of sub-processes, such an intensity correction, resembling, filtering, and so forth. In steps 54 and 56, anatomical markers in the image data 50 may be detected, and an image grid may be created. Based on the anatomical markers and the image grid, the data may undergo registration in a step 58. Following registration, features of interest in the image data 50 may be extracted in a step 60. While certain exemplary steps of the method 48 are presently described, it should be noted that the image data 50 may undergo registration or feature extraction through fewer, different, or additional steps in full accordance with the present technique.

In one embodiment, the image data 50 includes one or more images of a human brain that may be mapped to a Talairach coordinate system. In such an embodiment, the image data of the human brain, which may include an MR image or some other image, may be normalized to correct intensity variations and resampled, such as to a 256×256×128 internal matrix, for further processing. Also, in such an embodiment, the anterior and posterior commissures (AC-PC) of the brain image and other anatomical reference points may be identified to facilitate Talairach registration. The brain images of the image data 50 may be elastically registered, such as through warping, to the Talairach coordinate system to facilitate later representation, analysis, and diagnostics.

Figure 4:
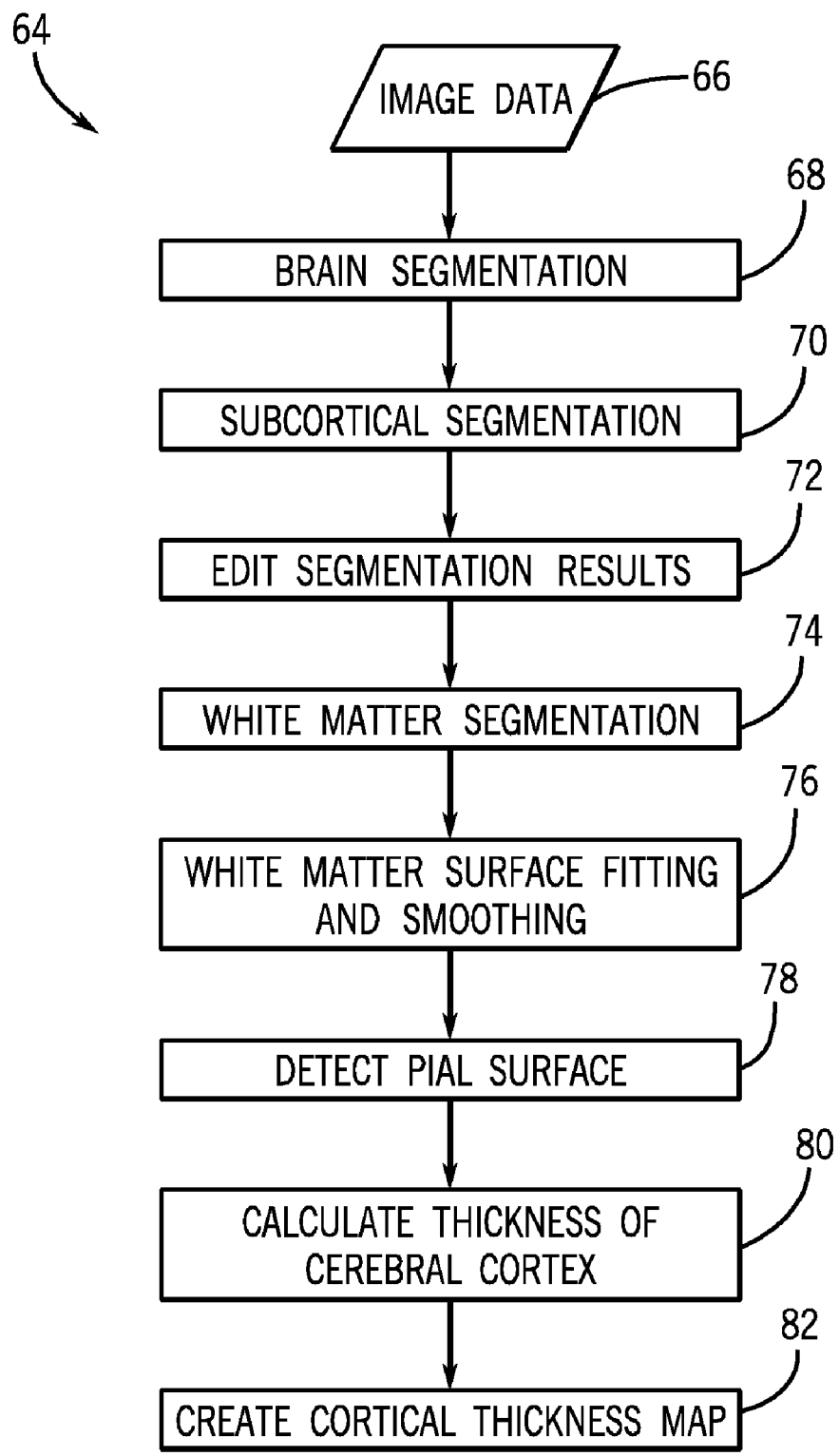
FIG. 4 is a flow chart of an exemplary method for creating a cortical thickness map from brain image data in accordance with one embodiment of the present invention.

It should be noted that the particular features that are of interest in the image data may vary depending on a particular disease or condition of interest. For example, in diagnosing neurological conditions, it may be useful to extract certain features of brain image data to facilitate diagnosis. Further, in some embodiments, it may be desirable to determine the thickness of the cerebral cortex of a patient or of one or more reference individuals. Accordingly, an exemplary method 64 for determining the cortical thickness of a brain from patient image data or reference image data, and for generating a cortical thickness map, is provided in FIG. 4 in accordance one embodiment of the present invention.

The method 64 may include a step 68 of segmenting brain tissue in image data 66 from other anatomical structures outside the brain, such as the skull. Further, in step 70, white matter of the brain and subcortical regions, such as ventricles may be segmented from the gray matter of the cerebral cortex. As the relative image intensities of the brain white matter and the other soft tissues may be very close or overlapped, in one embodiment the segmented brain may be manually edited to remove unwanted remaining tissue, or to restore inadvertently deleted cortical tissue, generally corresponding to a step 72. Further white matter segmentation, surface fitting, and smoothing may be performed in steps 74 and 76. In a step 78, the pial surface (i.e., the outside surface of the brain gray matter) may be detected. It should be noted that the pial surface generally includes numerous gyri and sulci, but may be considered to be smooth regionally to facilitate processing. The pial surface may be detected in various matters, such as through use of a deformable model or dilation from the surface of the white matter. The thickness of the cerebral cortex (i.e., the cortical thickness) may be calculated in a step 80, and a cortical thickness map visually depicting the cortical thickness may be created in a step 82.

In some embodiments, standardized reference cortical thickness maps may be calculated from image data collected from other persons or groups of persons (e.g., normal persons, persons diagnosed with Alzheimer's disease (AD), persons diagnosed with Parkinson's disease (PD), persons diagnosed with frontotemporal dementia (FTD), and so forth), and stored in large databases, such as those collected by the Alzheimer's Disease Neuroimaging Initiative (ADNI). Such standardized maps may serve as reference image data with respect to patient cortical measurements, and may be grouped and standardized according to any desired characteristic. For instance, in one embodiment, such data may be standardized based on a demographic characteristic, such as the race, gender, or age of the persons from which the data was collected. Such standardized data allows for the computation of average cortical thickness of normal patients and the thickness distribution across different function regions of the brain that affect memory, movement, speech, language, hearing, vision, sensation, emotion, and so forth. The average cortical thickness maps may be created from the reference image data, and also standardized according to age, gender, or race distributions, or according to any other characteristic of interest. While certain presently disclosed embodiments are described with respect to brain features, such as cortical thickness, it will appreciated that the present techniques may be applied more generally to any features of interest, including those of image data of other anatomical regions besides the brain.

Figure 5:
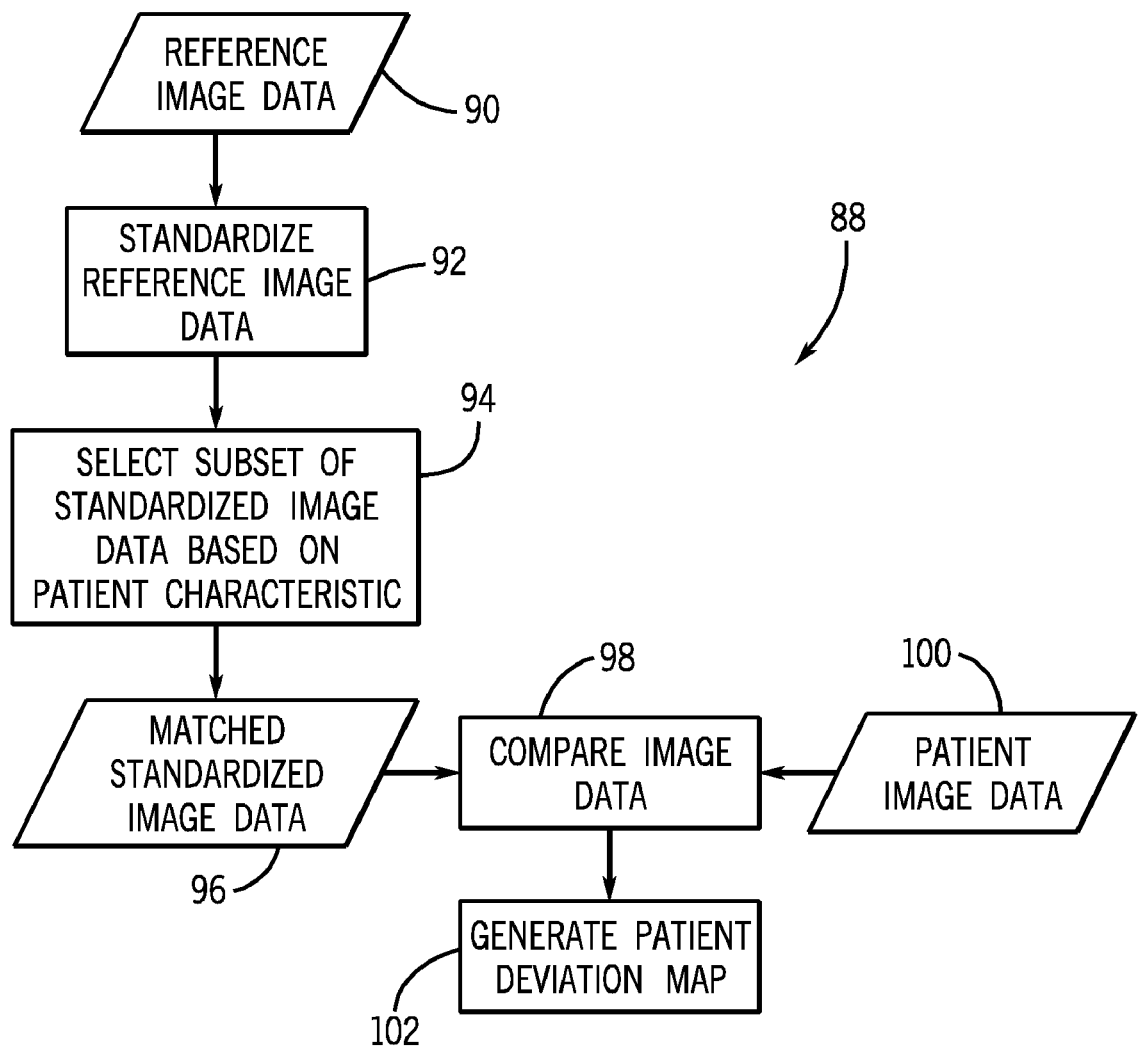
FIG. 5 is a flow chart of an exemplary method for generating deviation maps in accordance with one embodiment of the present invention.

In some instances, it may be desirable to also generate anatomical deviation maps, such as cortical thickness deviation maps, indicative of differences between a patient anatomical region and a reference anatomical region. As such, an exemplary method 88 for generating deviation maps from standardized reference data is illustrated in FIG. 5 in accordance with one embodiment of the present invention. In the presently illustrated embodiment, reference image data 90 is standardized in a step 92. As noted above, reference image data may be collected from a population of individuals and grouped or standardized according to one or more desired characteristics, such as age, gender, or race. While the presently illustrated embodiment is described with respect to image data, it is noted that reference non-image data and patient non-image data may also, or instead, be used to generate the deviation maps discussed herein in full accordance with the present technique.

The method 88 may include a step 94 of selecting a subset of the standardized reference image data based on a patient characteristic. For instance, if a patient is a sixty-five-year-old woman, a subset of the standardized reference image data grouped to include reference images pertaining to women between sixty and seventy years of age may be more relevant for comparative purposes than a group of standardized reference images composed of data collected from men between twenty and thirty years of age. Once a desired group of standardized image data is selected, the matched standardized image data 96 may be compared to image data 100 of the patient in a step 98. In other embodiment, non-image data of the patient may instead or also be compared to matched standardized non-image data, as described above. Additionally, the various data may be processed and standardized in any suitable manner to facilitate such comparisons.

Based on such comparison, a patient deviation map representative of the difference between the patient image data 100 and the standardized image data 96 may be generated in step 102. For example, with respect to cortical thickness, a patient cortical thickness map may be obtained through a comparison of the patient cortical thickness map with a standardized cortical thickness map based on a representative population of normal individuals. Consequently, in one embodiment, the patient cortical thickness deviation map may generally illustrate differences of the cortical thickness of the patient with respect to normal people of similar age, sex, or race. The deviation maps described herein may be generated through any suitable techniques. In one embodiment, a deviation map is a visual representation in which each point of the map represents a z-score generally corresponding to the number of standard deviations (based on a population) in the difference between a patient value and the average value (of the population) for that point. Although such deviation maps may be calculated from image data, it is noted that deviation maps may be created using one or more of numerical data, text data, waveform data, image data, video data, or the like.

The various anatomical region maps and deviation maps described herein may be visualized to facilitate further analysis or diagnosis. For instance, any or all of the standardized cortical thickness maps, the patient cortical thickness maps, the patient cortical thickness deviation maps, or standardized cortical thickness deviation maps (as described below) may be expressed as surface matrices, and can be displayed or overlaid on a three-dimensional (3D) brain surface, a pial surface, or an inflated brain surface.

Figure 6:
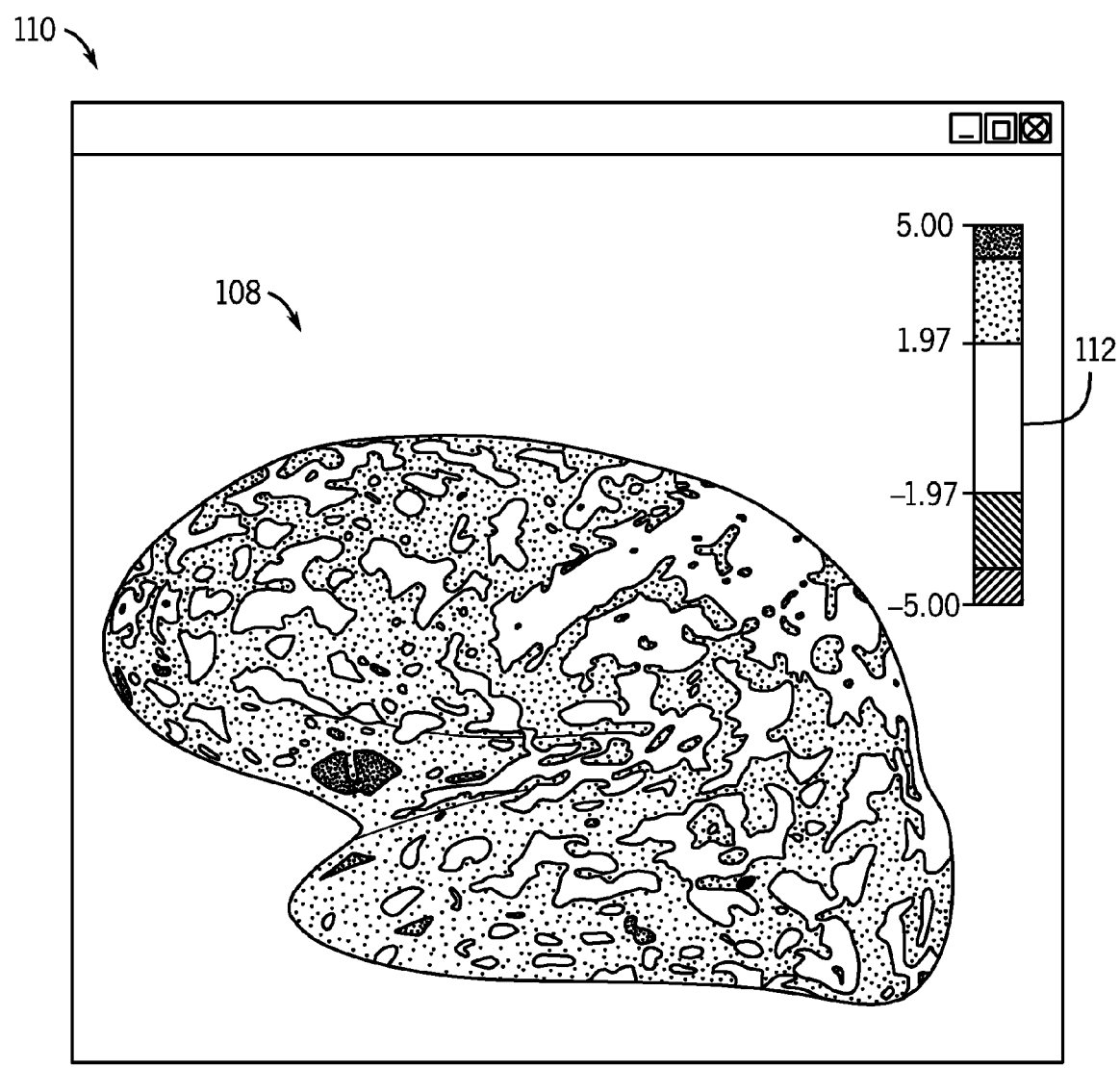
FIG. 6 is an exemplary visual mapping of cortical thickness data on an inflated brain surface in accordance with one embodiment of the present invention.

By way of further example, such an expression is illustrated in FIG. 6 in accordance with one embodiment of the present invention. Particularly, cortical thicknesses or deviations may be depicted on an inflated brain surface 108, as illustrated within window 110. Various regions of the brain 108 may be color coded according to a scale 112 to represent the cortical thickness, or deviation from normal thickness, to facilitate user-understanding of the represented anatomical information.

Figure 7:
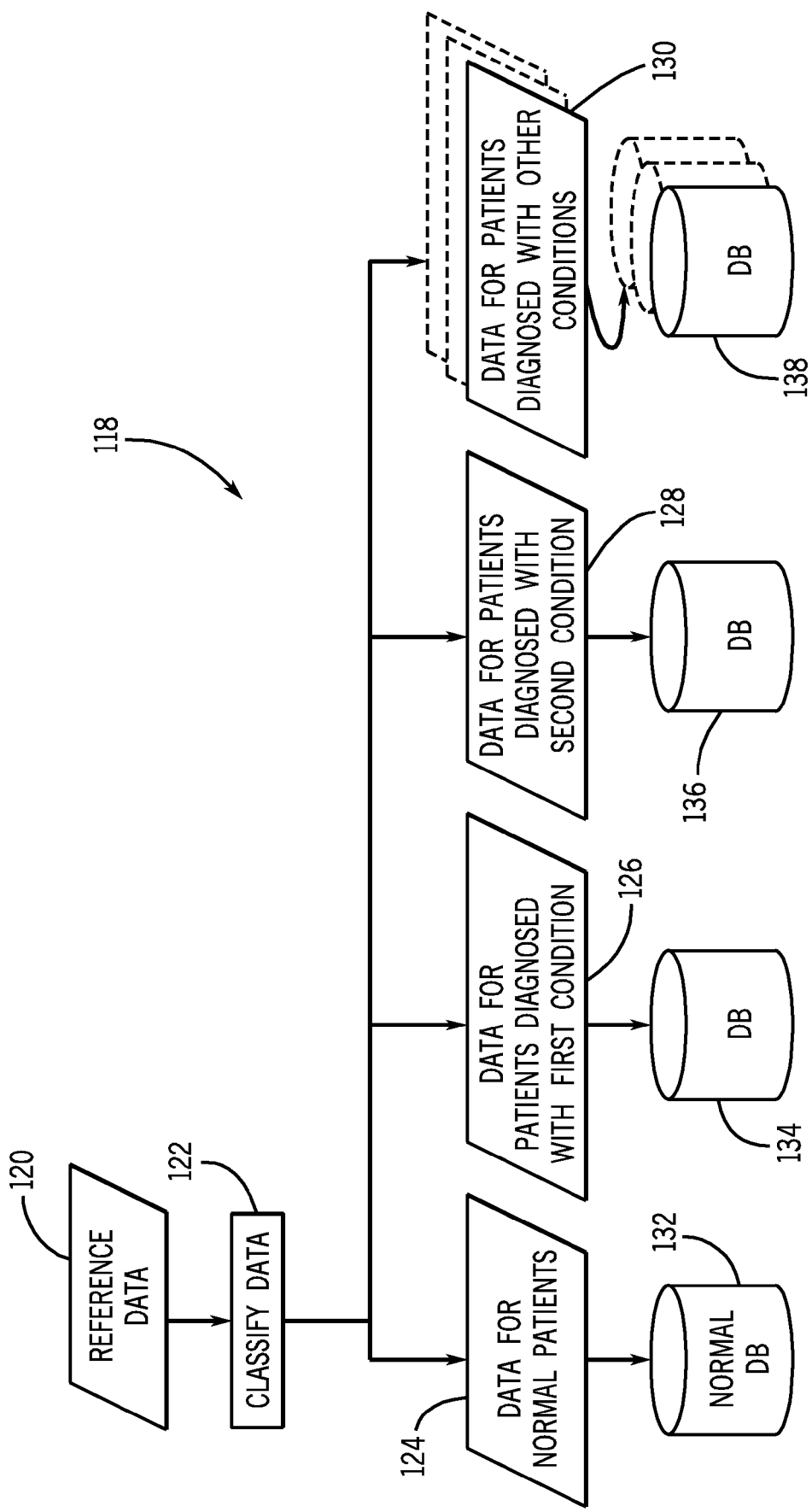
FIG. 7 is a block diagram representative of the division of reference data into standardized databases in accordance with one embodiment of the present invention.

Additionally, reference data may be classified and sorted into standardized databases, such as through an exemplary method 118 generally depicted in FIG. 7 in accordance with one embodiment of the present invention. The method 118 may include accessing reference data 120, which may include known population image data, and classifying such data in a step 122. For example, the reference data 120 may be classified into various groups, such as data 124 for normal patients; data 126 for patients clinically diagnosed with a first condition, such as Alzheimer's disease (AD); data 128 for patients diagnosed with a second condition, such as frontotemporal dementia (FTD); and data 130 for patients diagnosed with other conditions, such as Parkinson's disease (PD), Huntington's disease (HD), multi-infarct dementia (MID), diffuse cortical Lewy body disease (DLBD), normal pressure hydrocephalus, progressive supranuclear palsy (PSP), or the like. While certain brain disorders, brain image data, and brain deviation maps are presently discussed for the sake of explanation, it is again noted that the use of the present techniques with other, non-neurological data and disorders is also envisaged. The data 124, 126, 128, and 130 may be stored in respective databases 132, 134, 136, and 138. Such databases may be stored in one or more memory devices or in other suitable media.

Figure 8:
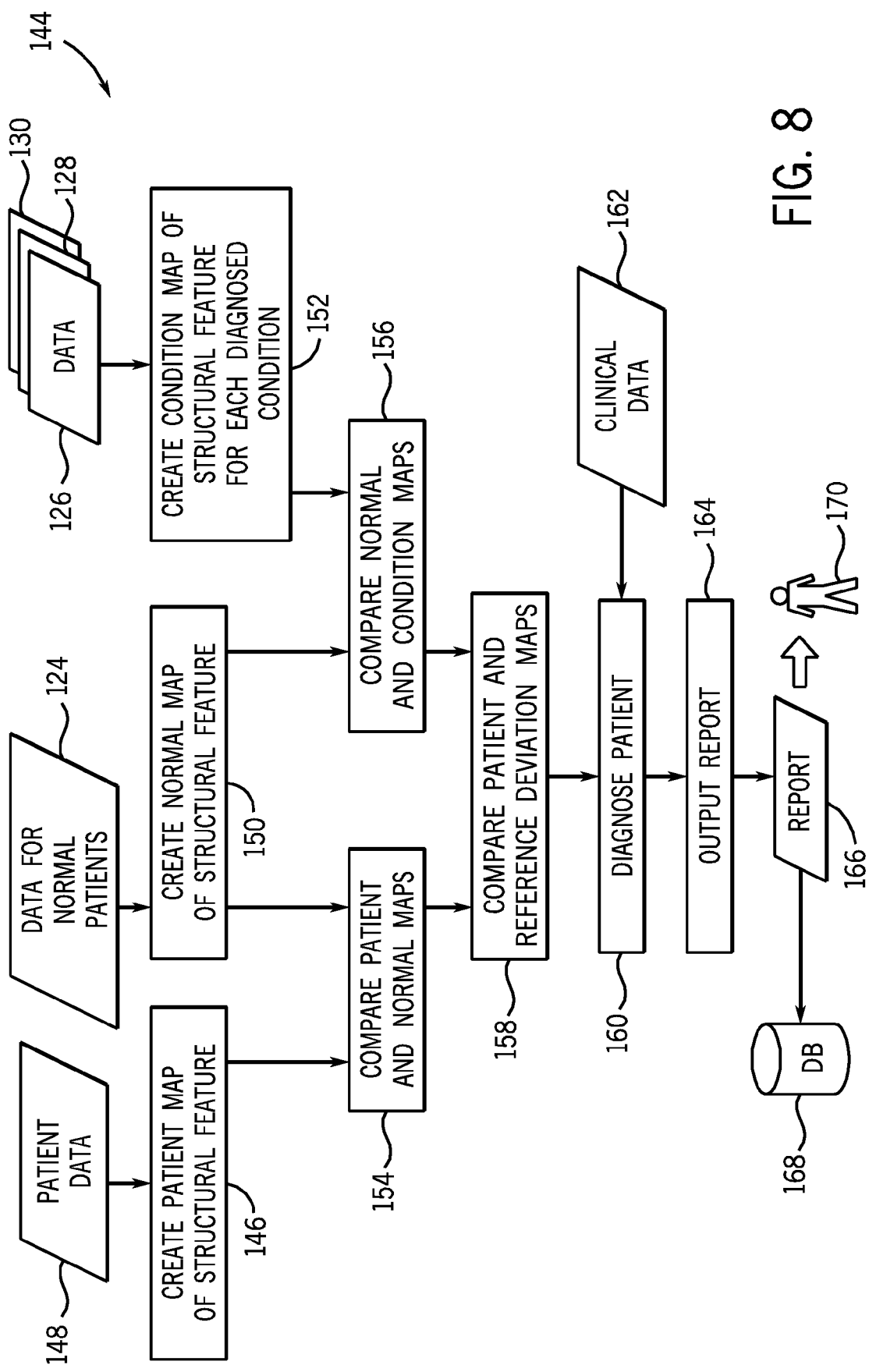
FIG. 8 is a flow chart of an exemplary diagnosis method in accordance with one embodiment of the present invention.

An exemplary method 144 for diagnosing a patient based at least in part on the foregoing data is illustrated in FIG. 8 in accordance with one embodiment of the present invention. The method 144 may include creating a patient map of a structural feature in a step 146, based on received patient data 148. In one embodiment related to brain disorders, the patient map created in step 146 may include a patient cortical thickness map. In a step 150, a normalized map of a structural feature is created based on the data 124 for normal patients. For instance, a standardized cortical thickness map for normal patients may be generated in this step. Although the presently illustrated embodiment is discussed with reference to maps of structural features, it is noted that maps of other features, such as functional or metabolic features, may also or instead be used in full accordance with the presently disclosed technique.

In a step 152, reference condition maps (e.g., average maps or other reference maps) of the structural feature may be created for each diagnosed condition or disorder, based on the reference data 126, 128, and 130 collected with respect to individuals of a population diagnosed with such conditions. For example, in one embodiment, representative average cortical thickness map may be calculated for each brain disorder of interest, such as AD, FTD, PD, or the like. Additionally, average maps (or other reference maps) corresponding to various severity levels within a disease type may also be generated. Thus, multiple representative or average maps may be created for each diagnosed condition or disease type.

The method 144 may also include a step 154 of comparing the patient and normal maps, and a step 156 of comparing the reference condition and normal maps. In one embodiment, the method 144 may include a step 158 of comparing one or more patient deviation maps (which may be generated from the comparison of step 154) with one or more disease reference deviation maps (which may be generated from the comparison of step 156). It is noted that the above-referenced maps, as well as other maps and data described herein, may be standardized into one or more common or similar formats to facilitate analysis and comparison. Also, it will be appreciated that the various maps described herein may be stored in one or more databases to facilitate subsequent data analysis. Additionally, any or all of the foregoing comparisons may be performed either automatically by a data processing system (e.g., system 32), or by a healthcare provider (e.g., a doctor), or by some combination thereof, to facilitate automatic or manual diagnosis of the patient in a step 160. Such diagnosis may also be based on additional data, such as clinical data 162, laboratory data, patient history, patient vital signs, results of various tests (e.g., functional tests, cognitive tests, neurological tests, or genetic tests), and so forth. Additionally, in a step 164 of the method 144, a report 166 may be output to a database 168 for storage, or to a user 170 in a human-readable format.

Figure 9:
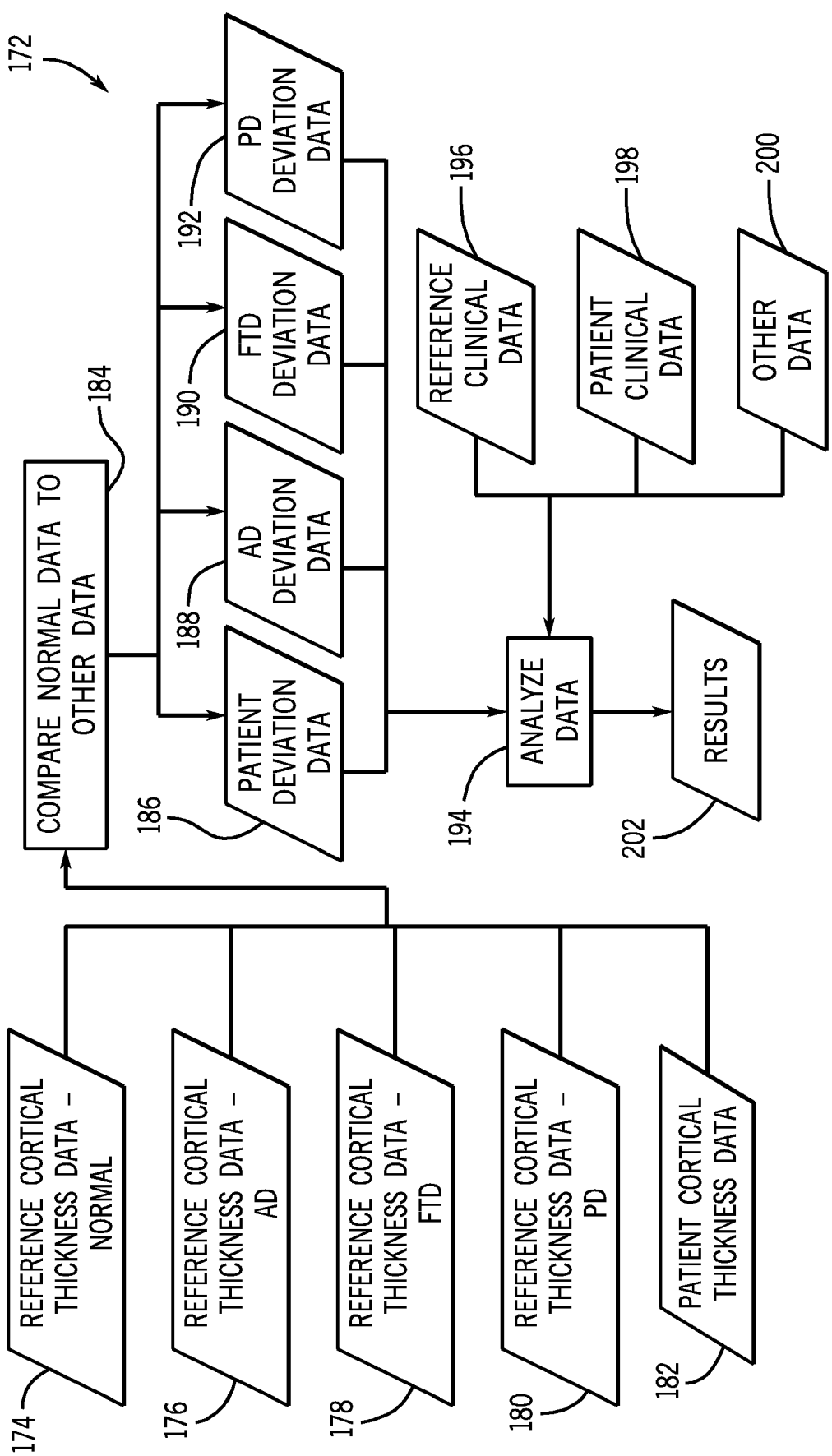
FIG. 9 is a flow chart of an exemplary method for creating and analyzing deviation data in accordance with one embodiment of the present invention.

Based on the patient and reference data and maps discussed above, numerous reference and patient deviation data and maps may be created. By way of example, an exemplary method 172 for creating and analyzing such deviation data is depicted in FIG. 9 in accordance with one embodiment of the present invention. The method 172 includes accessing reference cortical thickness data for: normal patients without diagnosed brain disorders (data 174), patients clinically diagnosed with AD (data 176), patients diagnosed with FTD (data 178), and patients diagnosed with PD (data 180). The method 172 may also include accessing patient cortical thickness data 182. It will be appreciated that, in other embodiments, the method 172 may access reference cortical thickness data for other brain disorders, which may be processed in a manner similar to those explicitly discussed in the present example. Indeed, the present processing techniques may also be applied to other disorders unrelated to the brain.

In a step 184, the normal data 174 may be compared to each of the other data 176, 178, 180, and 182, to generate patient deviation data 186, AD deviation data 188, FTD deviation data 190, and PD deviation data 192, all of which may represent deviations from the normal data 174. Such deviation data may include structural deviation maps, such as cortical thickness deviation maps, representative of differences between the patient data and the disease type reference data, on the one hand, and the normal reference data on the other. Additionally, the deviation data may also include functional deviation maps indicative of functional, rather than structural, differences between the patient (or reference data indicative of reference disease types) and normal individuals. In some embodiments, structural deviation maps may include cortical thickness deviation maps, and functional deviation maps may include cerebral blood flow rate deviation maps or metabolic rate deviation maps.

In step 194, such deviation data may be analyzed. For instance, in one embodiment, a patient cortical thickness deviation map may be compared to representative reference cortical thickness deviation maps for each of the above noted brain disorders to facilitate diagnosis of the patient with respect to one or more of such brain disorders. Additionally, reference clinical data 196, patient clinical data 198, and other data 200 may also be analyzed by a data processing system or a user to facilitate diagnosis. In one embodiment, such analysis may include pattern matching of patient maps and reference maps, and confidence levels of such matching may be provided to a user. Finally, results 202 of the analysis may be output to storage or to a user.

Figure 10:
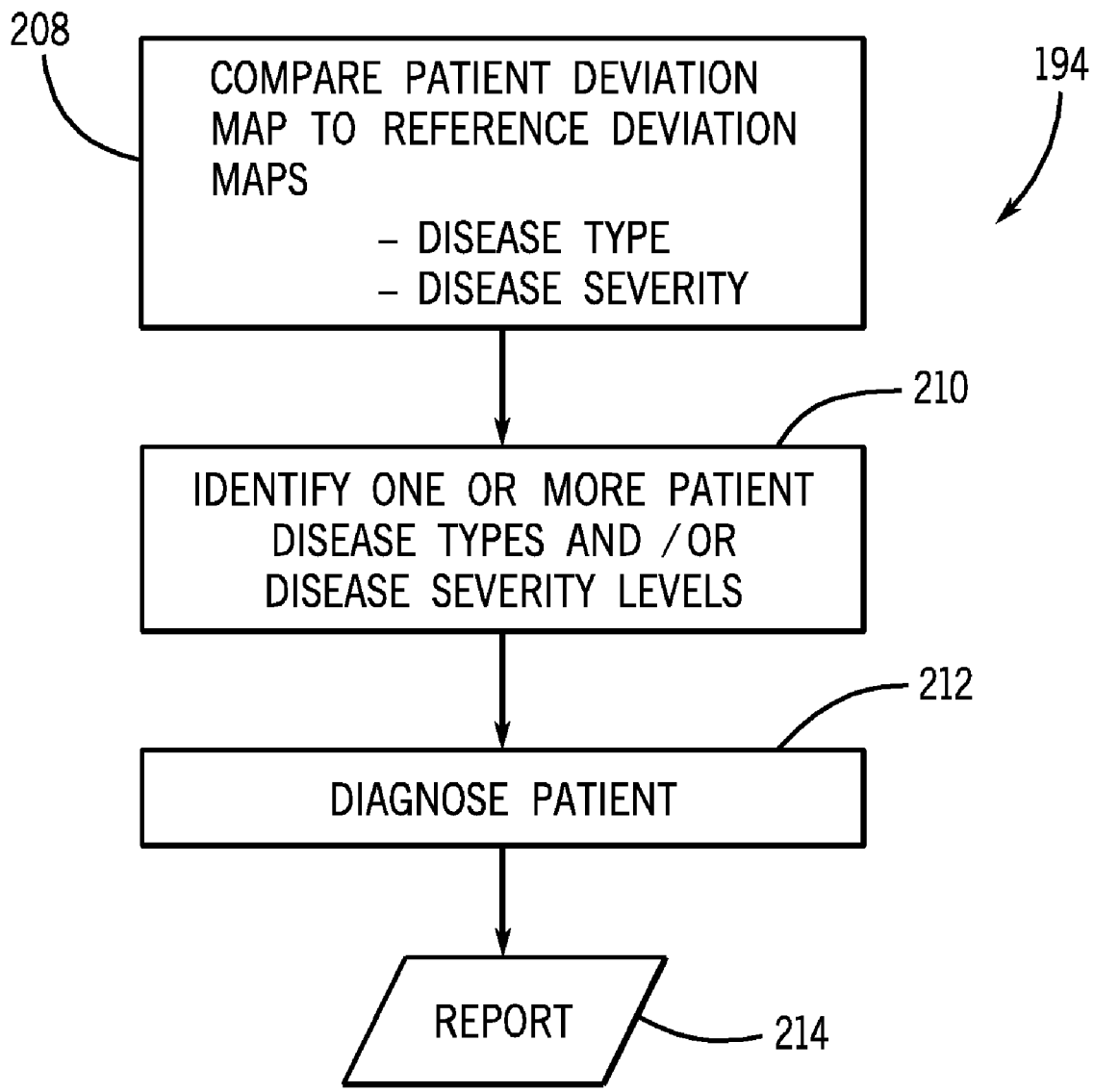
FIG. 10 is a flow chart of a method for diagnosing a patient based on comparison of a patient deviation map to reference deviation maps in accordance with one embodiment of the present invention.

A method 194 for analyzing the data discussed above and diagnosing a patient is illustrated in FIG. 10 in accordance with one embodiment of the present invention. In a step 208, one or more patient deviation maps, which may include a structural deviation map (e.g., a cortical thickness deviation map) or some other deviation map (e.g., a functional deviation map), may be compared to one or more reference deviation maps, such as those previously described. Notably, the reference deviation maps may include deviation maps (e.g., functional deviation maps or metabolic deviation maps or structural deviation maps) representative of one or more disease types, as well as various severity levels of the one or more disease types.

Based on such comparisons, one or more patient disease types and/or disease severity levels may be identified in a step 210 and diagnosed in a step 212. In some embodiments, such as a fully automated embodiment, steps 210 and 212 may be combined. In other embodiments, however, the identification and diagnosis may be performed as separate steps. For instance, the data processing system 32 may identify various potential disease types or severity levels and present the identified disease types or severity levels to a user for diagnosis. A report 214 may include an indication of the identified patient disease types or severity levels, the diagnosis, or both.

Figure 11:
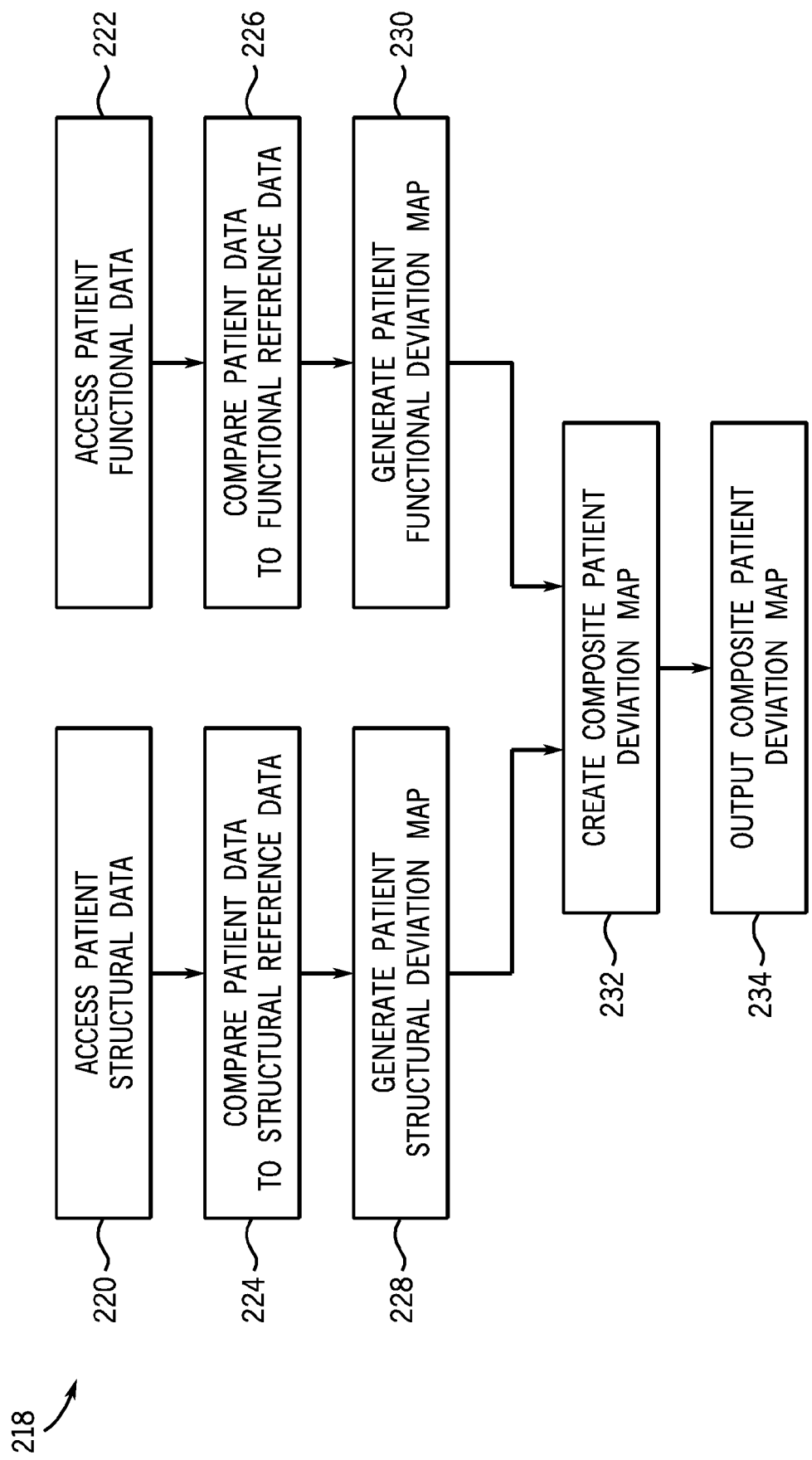
FIG. 11 is a flow chart of an exemplary method for generating a composite deviation map indicative of both structural and functional deviation in accordance with one embodiment of the present invention.

In some embodiments, it may be desirable to combine indications of functional deviations and structural deviations of a patient with respect to reference data and to output such deviations in a visual manner that facilitates efficient diagnosis of a patient by a healthcare provider. Accordingly, an exemplary method 218 for generating a composite deviation map indicative of both structural and functional deviation is depicted in FIG. 11 in accordance with one embodiment of the present invention. In the presently illustrated embodiment, the method 218 includes steps 220 and 222 for accessing structural and functional data, respectively, for a patient. The patient structural and functional data may include various image and non-image data with respect to an anatomical region of the patient. In one embodiment, the anatomical region may include the cerebral cortex of the patient. Additionally, the patient structural and functional data may include image data obtained from different imaging modalities.

The patient structural and functional data may be compared to standardized reference structural and functional data, respectively, in steps 224 and 226. As noted previously, reference data may be standardized according to any desired characteristics, such as, but not limited to, age, gender, or race. Based on such comparisons, one or more structural deviation maps for the patient may be generated in a step 228, and one or more patient functional deviation maps may be generated in a step 230. In one embodiment, the patient structural deviation map may indicate deviation of patient cortical thickness at one or more particular locations of the patient cerebral cortex with respect to expected thickness represented by the standardized reference data. In another embodiment, the patient structural deviation map may be generated via comparison of MR images of the patient and of the standardized reference data. Also, in a neurological context, the patient functional deviation map may indicate deviation of patient brain functioning, such as a cerebral blood flow rate or a metabolic rate, from standardized rates. It will, however, be appreciated that the deviation maps may be generated based on a wide array of image data and/or non-image data, as discussed above.

It is again noted that the patient structural deviation map may generally represent structural differences of an anatomical region of the patient with respect to standardized reference data for a similar anatomical region. For instance, in one embodiment, the patient structural deviation map may include a cortical thickness deviation map for the patient with respect to standardized cortical thickness data, such as described above. In turn, the patient functional deviation map may represent non-structural differences between a patient anatomical region and a corresponding anatomical region of standardized data. For example, in some embodiments, the patient functional deviation map may be indicative of differences in metabolic activity or other functional activity between the patient and standardized reference data. To facilitate easy and efficient communication of such differences to a user, a composite patient deviation map, indicative of both the functional and structural differences discussed above, may be created in a step 232.

The patient structural deviation map and the patient functional deviation map, along with any other additional deviation maps, may be combined in any suitable fashion to create the composite patient deviation map. For instance, in one embodiment, the individual patient deviation maps may be overlain to create a single composite patient deviation map indicative of multiple deviations of the patient with respect to standardized data. In another embodiment, the individual patient functional and structural deviation maps may be combined through an image fusion process. Particularly, in one embodiment, the patient structural deviation map may be generated through comparison of patient image data and standardized image data each of a first imaging modality, while the patient functional deviation map is generated from image data (of both the patient and standardized reference sources) obtained through a second imaging modality different than the first. For example, structural deviations identified through comparison of MR images may be combined with functional deviations obtained from PET image data to generate a single composite patient deviation map indicative of both functional and structural deviations. In another embodiment, the patient structural deviation map based on a first criterion (e.g., cortical thickness from MRI images) can be combined with the patient structural deviation map based on a second criterion (e.g., medial temporal lobe atrophy from CT images). In yet another embodiment, the patient functional deviation map based on a first criterion (e.g., FDG, a well known PET tracer uptake in PET images) can be combined with the patient functional deviation map based on a second criterion (e.g., uptake of PIB, a well known tracer for beta-amyloid in PET images).

Additionally, different colors may be used to indicate and contrast structural differences and functional differences. For example, in one embodiment, functional deviations may generally be depicted in a composite patient deviation map by the color red, while structural deviations may generally be indicated through use of the color blue. Additionally, the magnitude of such deviations may be represented by various shades of red or blue to allow a doctor or other user to quickly ascertain patient deviations and the magnitudes of such deviations, as well as to facilitate diagnosis of the patient. It will be appreciated, however, that other or additional colors may also be used to indicate the different types of deviations and their relative magnitudes.

The method 218 may also include outputting the composite patient deviation map in a step 234. In some embodiments, outputting the composite patient deviation map may include storing the composite patient deviation map in a memory device. In other embodiments, outputting the composite patient deviation map may also, or instead, include providing the composite map to a user in a human-readable format, such as by displaying the composite patient deviation map on a display or printing a physical copy of the composite patient deviation map. Also, the presently illustrated embodiment is currently represented as a parallel process with respect to the generation of separate patient structural and functional deviation maps. It is noted that, while the present exemplary method is described for explanatory purposes as a parallel process, the steps of any of the methods described herein may be performed in any suitable manner, and are not limited to being performed in any particular order or fashion.

Figure 12:
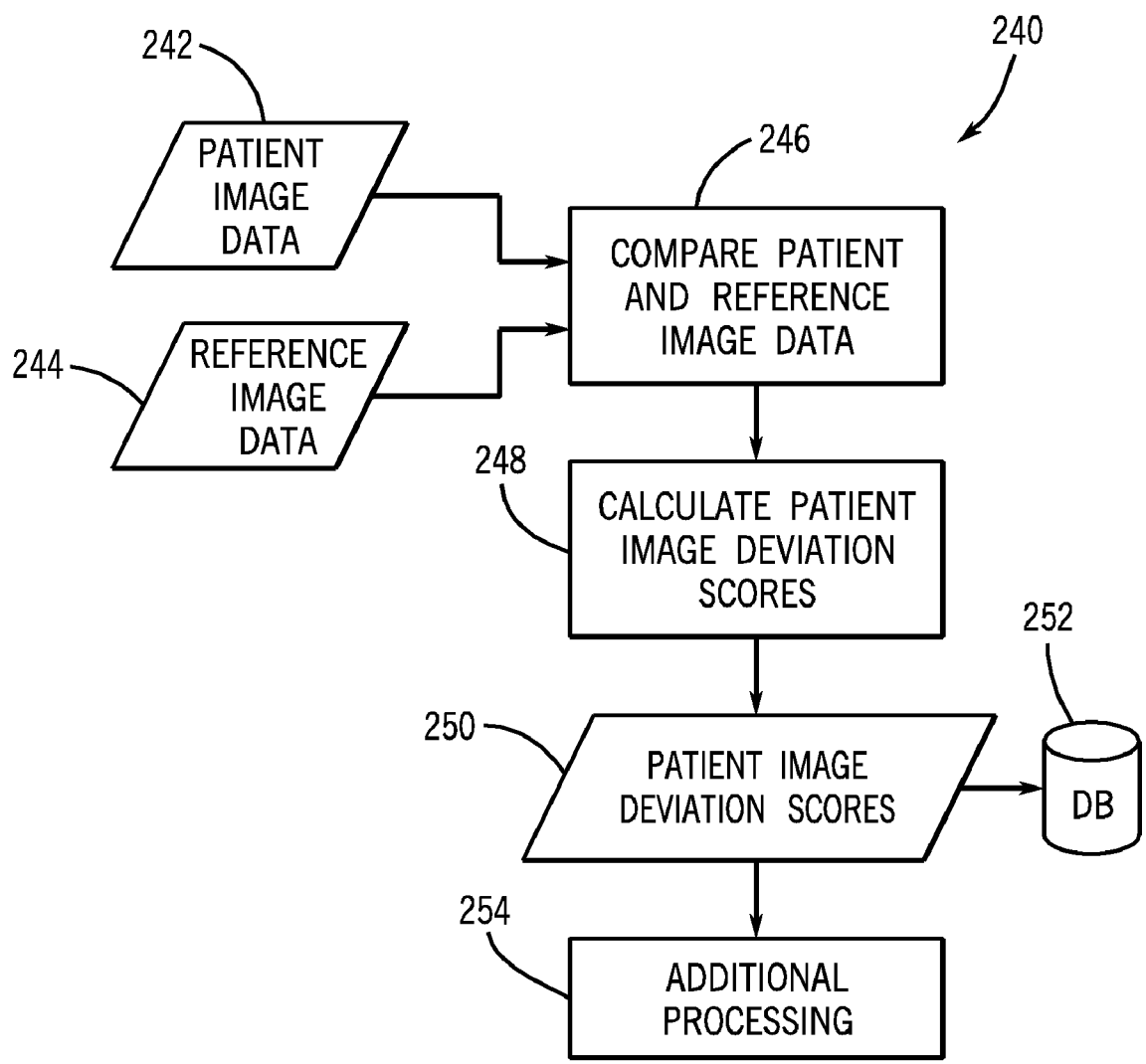
FIG. 12 is a flow chart of a method for generating image deviation scores for a patient in accordance with one embodiment of the present invention.
Figure 13:
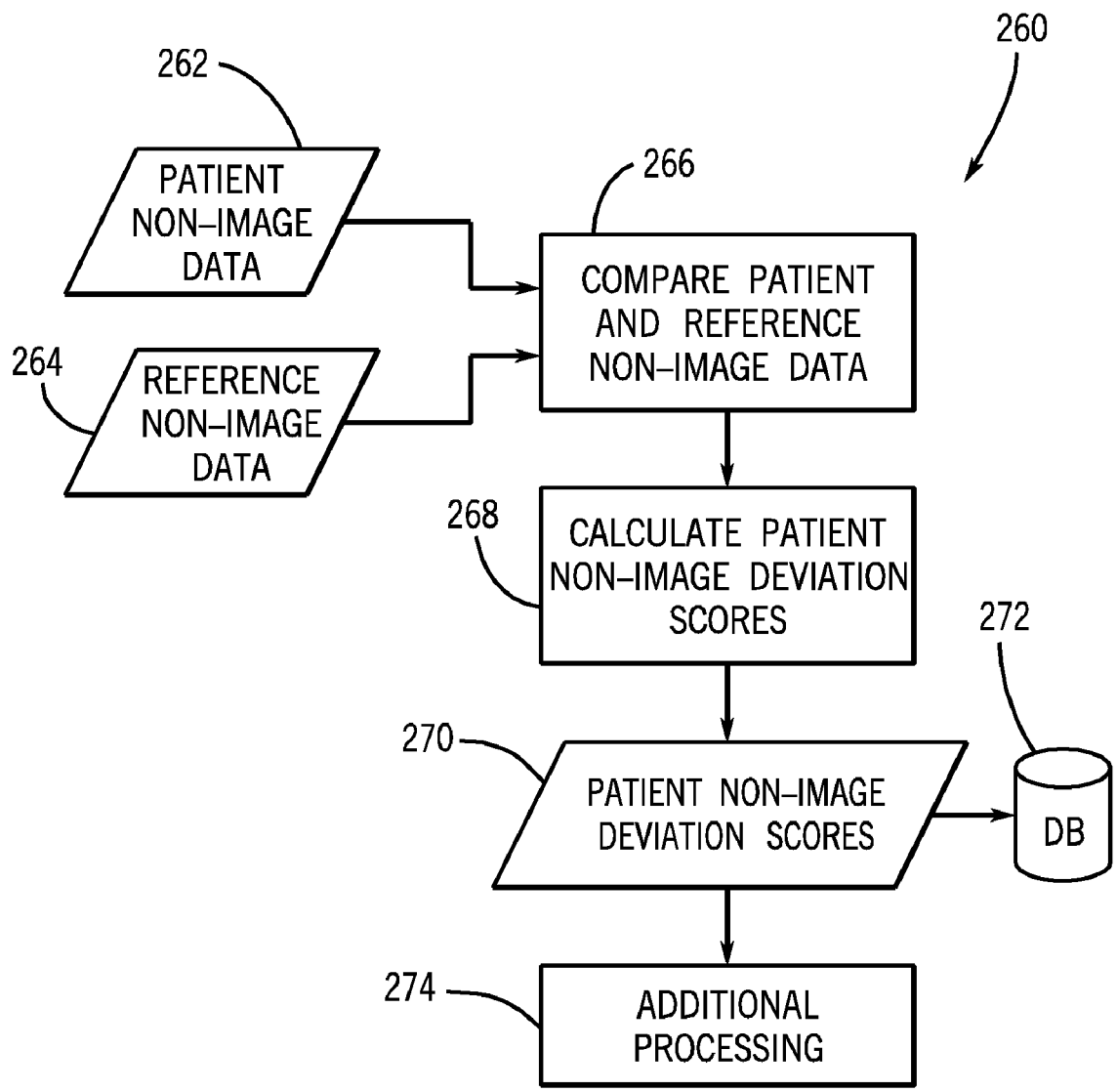
FIG. 13 is a flow chart of a method for generating non-image deviation scores for a patient in accordance with one embodiment of the present invention.

The extent of patient deviation from standardized data may also be translated into one or more deviation scores, which may, in one embodiment, be generated through the methods generally depicted in FIGS. 12 and 13. An exemplary method 240 of FIG. 12 may include accessing patient image data 242 and reference image data 244. Such image data may be received from any suitable source, such as a database or an imaging system. Indeed, the image data 242 and 244 may include image data from a variety of modalities and collected from a wide range of sources. The reference image data 244 may be standardized according to any desired characteristics. For instance, in one embodiment, the reference image data 244 may generally represent features of normal individuals with certain demographic characteristics (e.g., characteristics similar to the patient). In a step 246, the patient image data 242 and the reference image data 244 may be compared to determine deviations of the patient image data 242 from the reference image data 244. In one embodiment, such differences may generally represent deviation (e.g., structural or functional differences) of the patient from normal individuals.

The method 240 may also include a step 248 of calculating one or more patient image deviation scores for differences between the patient image data 242 and the reference image data 244. Such deviation scores may be indicative of an array of functional or structural deviations of the patient with respect to reference image data, including deviations in metabolic activity (e.g., fluorodeoxyglucose (FDG) metabolism, which may be observed in PET images), physical anatomy (e.g., cortical thickness, which may be measured in MR images), and functional activity (e.g., Pittsburgh Compound-B (PIB) measure, which may be determined from PET images), to name but a few. The patient image deviation scores may be calculated in various manners, such as based on projection deviation, single pixel (2D) deviation, single voxel (3D) deviation, or on any other suitable technique. The calculated patient image deviation scores 250 may then be stored in a database 252, output to a user, or may undergo additional processing in one or more further steps 254.

Turning to FIG. 13, an exemplary method 260 for calculating non-image deviation scores may include accessing patient non-image data 262 and reference non-image data 264. The non-image data may be received from any suitable source, such as a database, a computer, or patient monitor. The patient non-image data 262 may include any non-image information collected for the purpose of diagnosing the patient, such as clinical data, laboratory data, patient history, patient vital signs, and the like, and may also include results of functional tests, cognitive tests, neurological tests, genetic tests, and so forth. The non-image data 264 may include similar data, which may be standardized based on one or more population or sample characteristics. Further, in one embodiment, the patient non-image data 262 and reference non-image data 264 may include one or both of numeric data and enumerated data (each of which may be continuous or discrete). The reference non-image data 264 may be data representative of features of normal persons with desired demographic characteristics (e.g., characteristics similar to the patient). In a step 266, the patient non-image data 262 may be compared to the reference non-image data 264 to identify differences between the data. In one embodiment, such differences may generally represent deviation (e.g., structural or functional differences) of the patient from normal individuals.

Additionally, the method 260 may include a step 268 of calculating one or more patient non-image deviation scores for differences between the patient non-image data 262 and the reference non-image data 264. It is noted that various techniques may be used to calculate the patient non-image deviation scores, including z-score deviation or distribution analysis. Of course, it will be appreciated that other calculation techniques may also or instead be employed in other embodiments. The calculated patient non-image deviation scores 270 may be stored in a database 272, output to a user, or may undergo additional processing in one or more further steps 274.

Figure 14:
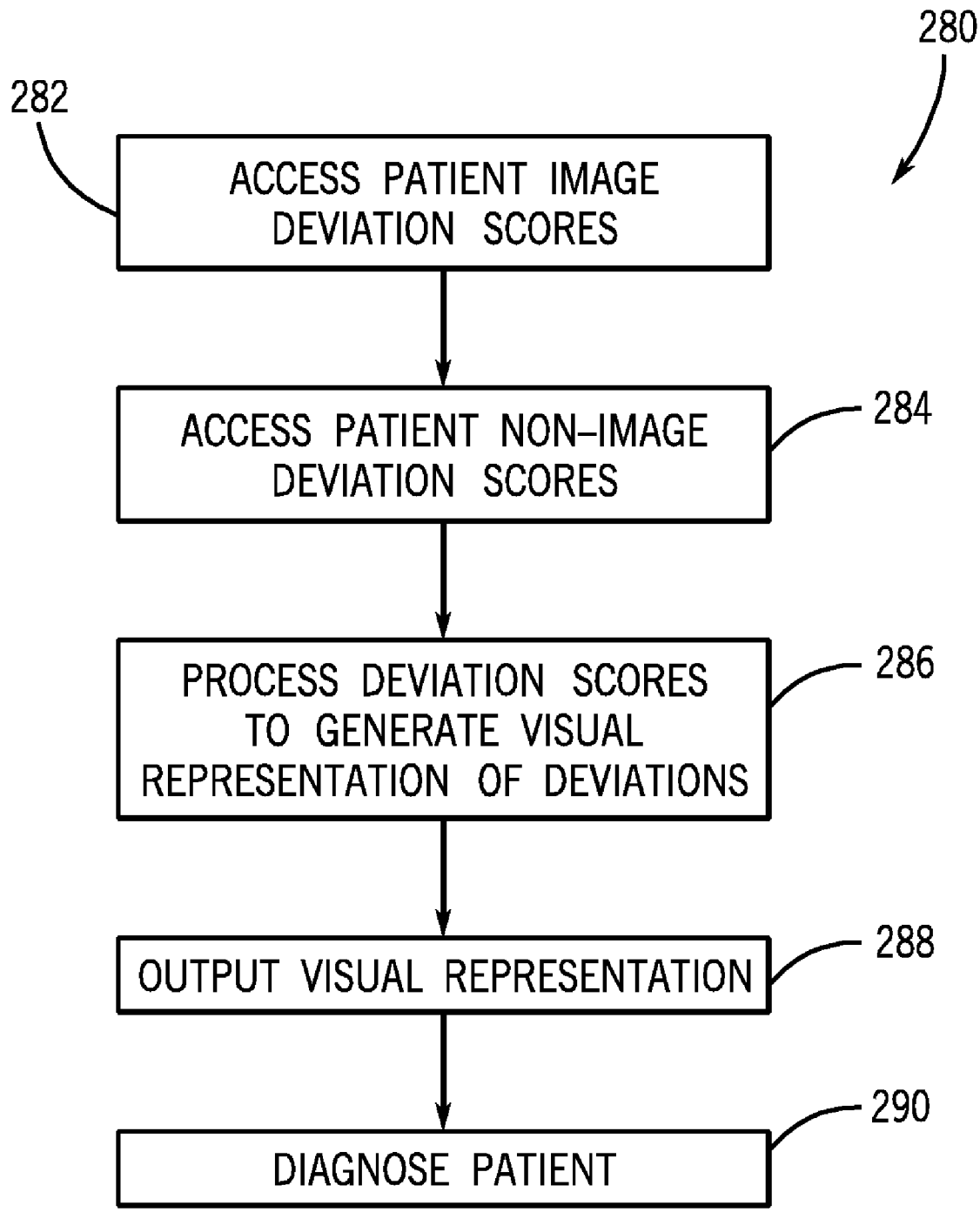
FIG. 14 is a flow chart of an exemplary method for generating a visual representation of patient deviation data based on deviation scores in accordance with one embodiment of the present invention.

An exemplary method 280 for accessing patient deviation scores and generating one or more visual representations to facilitate patient diagnosis is generally provided in FIG. 14. The method 280, in one embodiment, includes accessing one or more patient image deviation scores and one or more patient non-image deviation scores in steps 282 and 284, respectively. These deviation scores may be processed, in a step 286, to generate a visual representation of the differences represented by the patient deviation scores. In one embodiment, patient deviation scores may be derived from dynamic data (e.g., video) or longitudinal data (e.g., data acquired at discrete points in time over a given period), and multiple visual representations corresponding to deviations at different points of time may be generated in step 286. The one or more visual representation may then be output, in a step 288, to facilitate diagnosis of the patient in a step 290. For deviations derived from dynamic or longitudinal data, multiple visual representations may be output simultaneously or sequentially.

Figure 15:
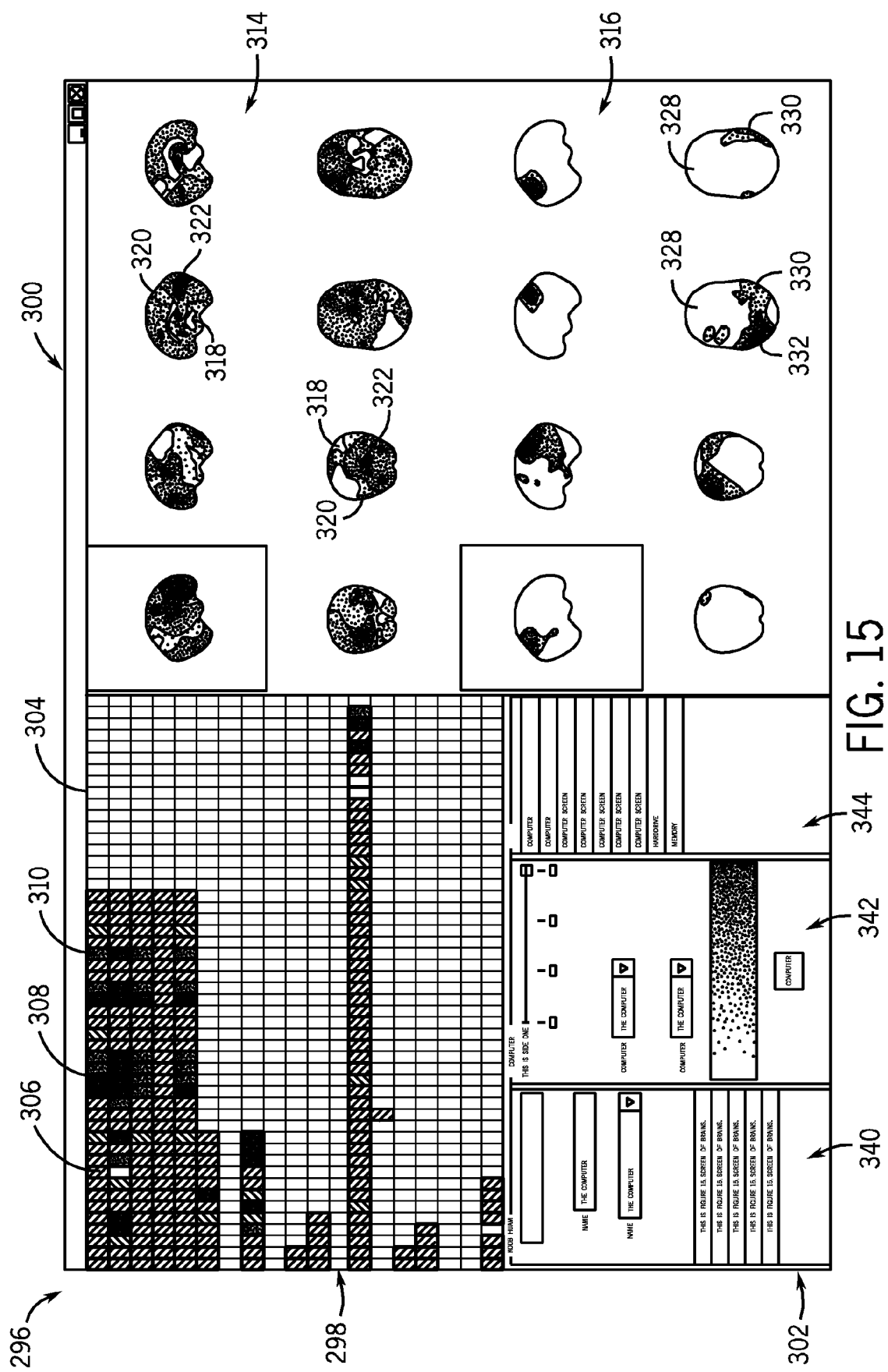
FIG. 15 illustrates an exemplary visual representation of a variety of patient deviation data in accordance with one embodiment of the present invention.

In some embodiments, the visual representation generally includes a combination and visualization of the various differences represented by the deviation scores, thus providing a holistic view of patient variance with respect to standardized data. By way of example, an exemplary visual representation 296 is depicted in FIG. 15 in accordance with one embodiment of the present invention. It is noted, however, the presently illustrated embodiment is provided merely for explanatory purposes, and that other visual outputs may take different forms.

In the presently illustrated embodiment, the visual representation 296 includes a region 298 for visualization of patient non-image deviation data maps, a region 300 for visualization of patient image data deviation maps or other image data, and a control panel 302. In various embodiments, numerous display techniques may be used to make the visualized deviation maps or other results more intuitive to a user, and to more clearly convey the extent of deviation (i.e., abnormality) of the results of the specific patient under review. Such display techniques, may include, as depicted in the presently illustrated embodiment, color mapping of image pixels or voxels, and color coding of individual cells in a table, wherein the color-coded cells each correspond to a particular clinical test result and the color of the cell corresponds to the magnitude of deviation of the patient result in comparison to standardized data. Additional display techniques may also include temperature gauges, spider graphs, dials, font variations, annotation, and the like.

The exemplary visual representation 296 includes a plurality of cells 304, at least some of which include patient non-image deviation maps associated with respective clinical test results and are color-coded to give a visual indication of the extent of deviation of the patient from reference data for each test. For instance, cell 306 may be associated with a functional test and shaded in a color that generally represents the magnitude of the deviation of the result of the functional test for the patient in comparison to standardized results for the functional test. Similarly, cells 308 and 310 may be associated with a cognitive test and a blood sugar test, respectively, and may be filled with particular colors to indicate the magnitude of deviations of the patient results for such tests from standardized result data. Although the present illustration depicts discrete color shades for the various cells, it will be appreciated that a continuous color range may instead be used, and that any one or more desired colors may be employed to efficiently communicate the extent of deviation of various clinical tests to a user. Additionally, it is noted that the patient deviation maps displayed in the cells 304 may be based on any suitable patient test having numerical or enumerated results that can be compared to standardized data, and such maps are non limited to those explicitly discussed herein.

Various image data may be displayed in a region 300 of the exemplary visual representation 296. In the presently illustrated embodiment, a plurality of structural patient deviation maps 314 and functional patient deviation maps 316 are illustrated in the top and bottom portions, respectively, of the region 300. These patient deviation maps may include various coloring or shading to denote deviation of a patient anatomical region with respect to standardized data. For instance, regions 318, 320, and 322 in the structural patient deviation maps 314 may generally correspond to portions of the patient brain exhibiting no or little deviation from the standardized data, portions exhibiting moderate deviation, and portions exhibiting severe deviation, respectfully. In embodiments pertaining to the human brain, such structural patient deviation maps 314 may include patient cortical thickness deviation maps, which may be generated from MR image data. It is again noted, however, that the presently disclosed techniques are not limited to cortical thickness deviation data, or to brain images. Rather, the presently disclosed techniques may be broadly applied to facilitate quantification, visualization, and diagnosis of a wide array of diseases and conditions.

The functional patient deviation maps 316 may also include variously colored regions to indicate the magnitude of deviation of that region for the patient with respect to standardized data. The functional patient deviation maps 316 may include, among other things, cerebral blood flow deviation or metabolic rate deviation of patient data from the standardized data, and may, in one embodiment, be generated from PET image data. In these maps 316, regions 328 may correspond to no or little deviation from the standardized data, while regions 330 and 332 may signify minor and major deviations, respectively, of the patient from the standardized data. The use of three different illustrative regions in the structural patient deviation maps 314 and functional patient deviation maps 316 is used for the sake of clarity and for explanatory purposes. It should be appreciated that other colors or shading may be used instead of or in addition to those illustrated herein, and such coloring or shading may be provided in a continuous range or provided at discrete levels.

The control panel 302 may facilitate presentation of other data to a user and user-control of certain visualization processes. For instance, in the presently illustrated embodiment, patient information may be displayed in a region 340, population information and selection control may be provided in a region 342, and various system parameters, test data, or other information may be provided in a region 344. In one embodiment, the population region 342 may allow a user to select a particular set of standardized data from a library of standardized data groups based on a desired characteristic. For instance, a user may enter one or more of a desired age range, gender, or race, and the system may then display visual representations of patient deviations from the selected standardized data set. In other words, in such an embodiment, the user may select demographic characteristics of the population segment of the standardized data to which the patient will be compared for purposes of visualizing deviation. Consequently, in one embodiment, the user may chose to visualize patient results as a measure of deviation from a particular standardized data set demographically matched to the patient.

Although the exemplary visual representation 296 includes graphical representations of structural and functional deviations in image data, as well as deviations with respect to non-image data (e.g., clinical tests, laboratory tests, and so forth), other visual representations having different data, or only subsets of the deviation data visualized above, may be generated in other embodiments. For instance, in certain embodiments the generated visual representation may only include representations of deviation with respect to either image data or non-image data, rather than both.

Figure 16:
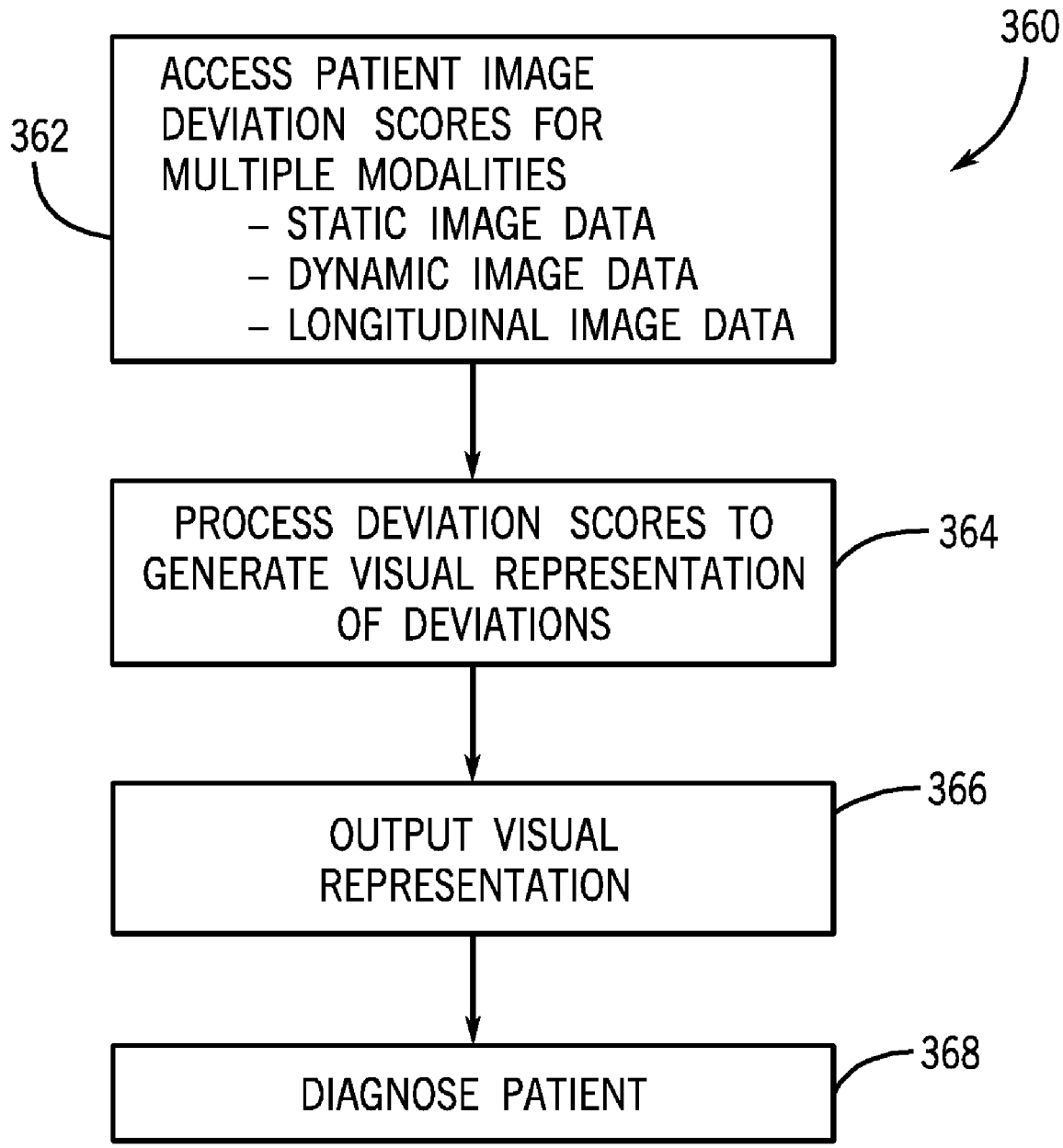
FIG. 16 is a flow chart of an exemplary visualization method in accordance with one embodiment of the present invention.

For example, a visualization method 360 is illustrated in FIG. 16 in accordance with one embodiment of the present invention. The method 360 may include a step 362 of accessing patient image deviation scores for multiple imaging modalities, such as CT, MR, PET, SPECT, digital tomosynthesis, or the like. The patient image deviation scores may be calculated through a comparison of patient image data to standardized reference image data pertaining to a population of individuals, as generally described above. Further, in various embodiments, the patient image deviation scores may be computed through comparison of patient static image data or patient dynamic image data (e.g., video) acquired in a single imaging system, or of patient longitudinal image data acquired over multiple imaging sessions, to reference image data of a similar or different type (i.e., static, dynamic, or longitudinal). The accessed patient image deviation scores may be processed in a step 364 to generate a visual representation of patient deviation with respect to the standardized image data, as generally discussed above. The generated visual representation may be output in a step 366 to facilitate diagnosis of the patient in a step 368.

Figure 17:
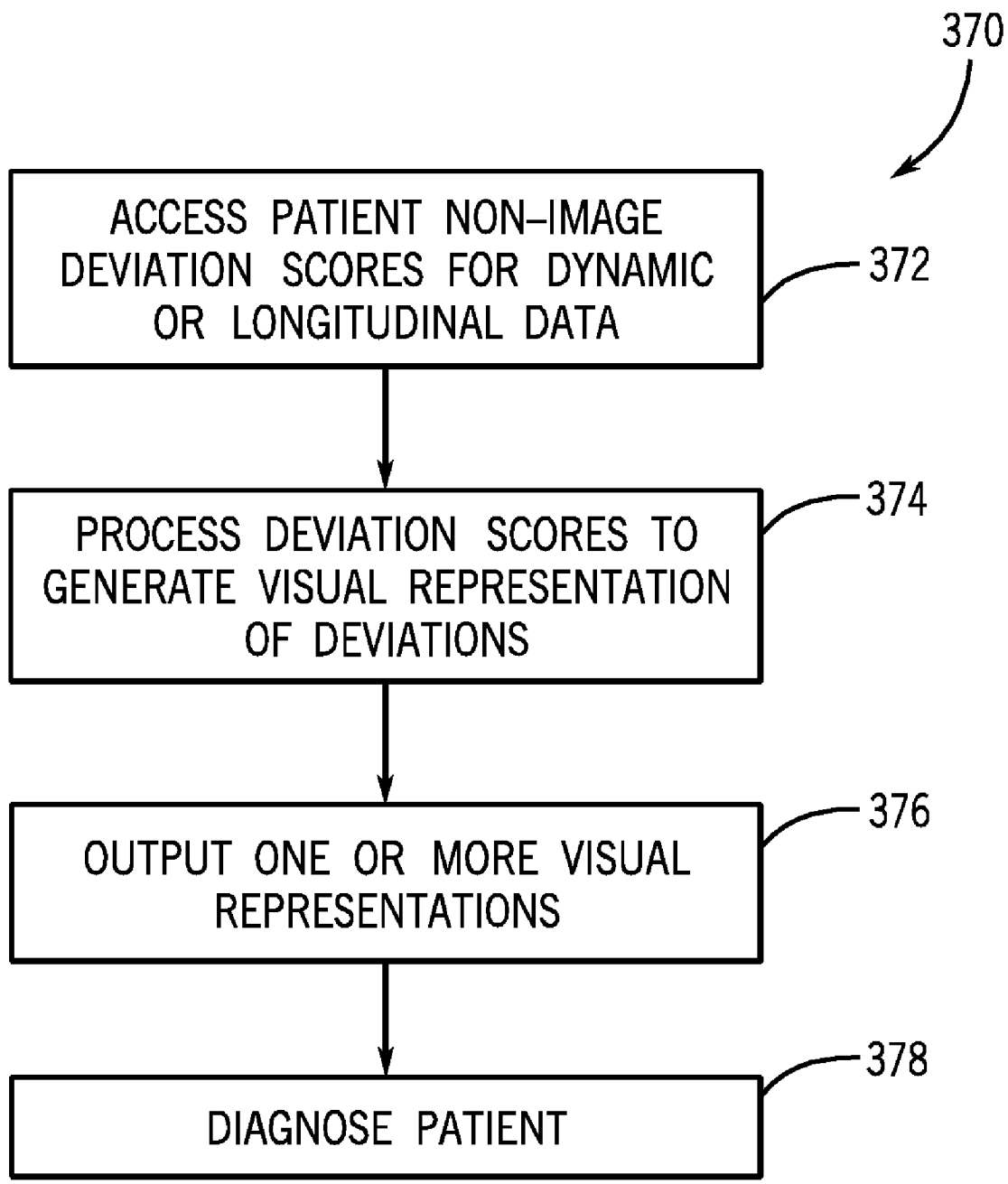
FIG. 17 is a flow chart of a different exemplary visualization method in accordance with one embodiment of the present invention.

An additional exemplary visualization method 370 is generally depicted in FIG. 17. The method 370 may include accessing patient non-image deviation scores for dynamic or longitudinal data in a step 372. Dynamic non-image data may include a substantially continuous series of clinical test results over a given period of time, while non-image longitudinal data may include test results (or groups of test results) obtained in a staggered fashion (e.g., such as at 3 month intervals) over multiple data acquisition sessions. As generally noted above, the patient non-image deviation scores for such data may be calculated based on comparison of patient non-image data to standardized non-image data. In some embodiments, the patient non-image data on which the deviation scores are based may include non-image data from different modalities (e.g., cognitive data, neurological data, and the like). The patient non-image deviation scores may be processed in a step 374 to generate one or more visual outputs indicative of deviation of the patient non-image data from the standardized non-image data. For instance, in one embodiment, a plurality of visual outputs may be generated based on comparison of a sequence of longitudinal patient non-image data to standardized non-image data. The visual representations may then be output in a step a 376 to facilitate diagnosis of the patient in a step 378. Multiple generated visual representations may be output simultaneously or sequentially.

Figure 18:
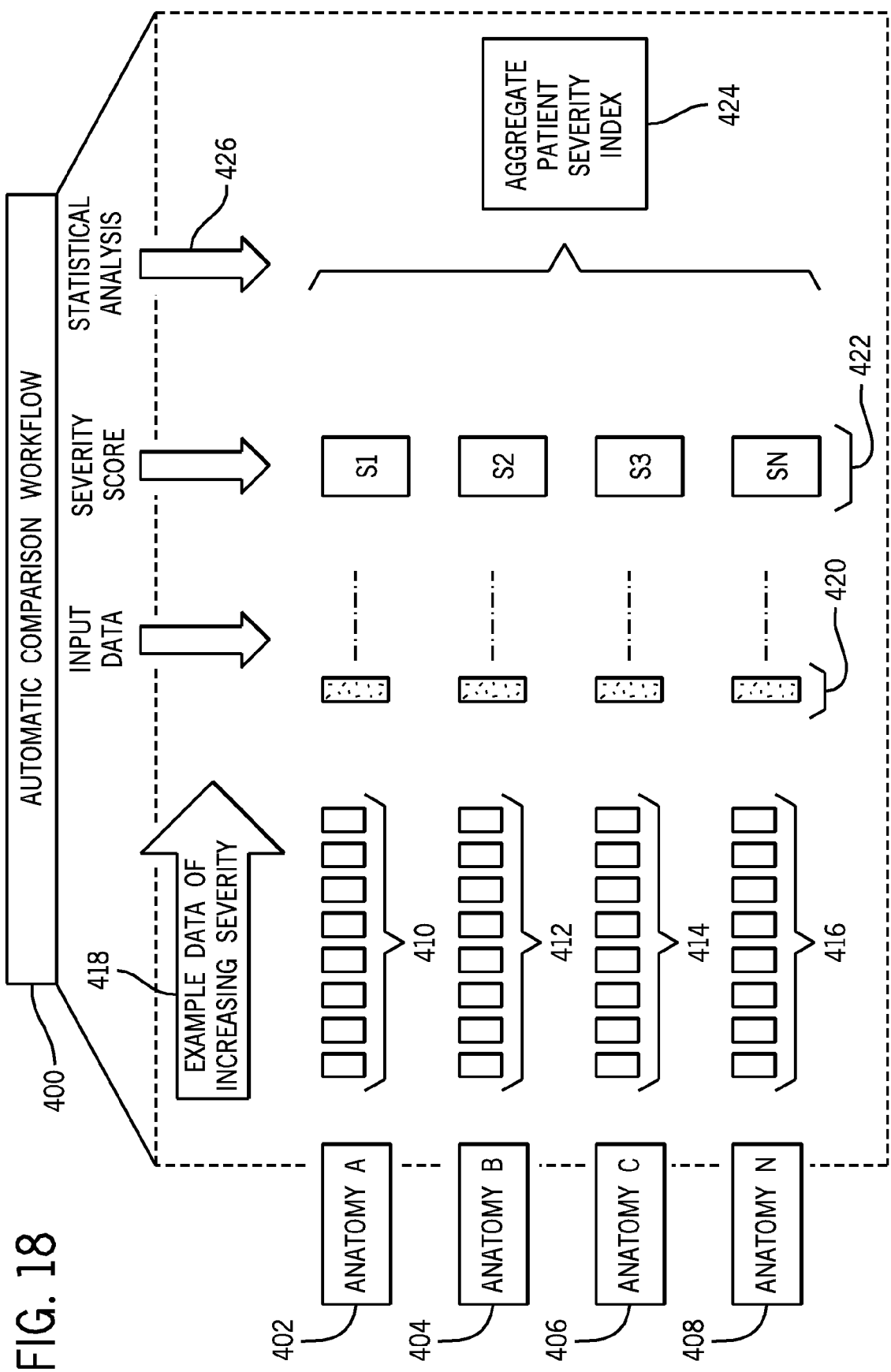
FIG. 18 is a diagram of an automatic comparison workflow to determine a severity index in accordance with one embodiment of the present invention.

FIG. 18 is an exemplary diagram of an automatic comparison workflow 400 generally depicting the automatic generation of a severity index for various anatomical features of interest. The automatic comparison workflow 400 may encompass a number of anatomical features, such as structural or functional features of a brain, a heart, or the like. To depict the possibility of such a multitude of anatomical features in a comparison, the automatic comparison workflow 400 is depicted as including a first anatomical feature "A" 402, a second anatomical feature "B" 404, a third anatomical feature "C" 406, an "N'th" anatomical feature "N" 408, and so forth. The automatic workflow comparison of FIG. 18 represents a specific implementation of the more generalized matching and presentation techniques described in U.S. Patent Application Publication No. 2007/0078873 A1, published on Apr. 5, 2007, and entitled "COMPUTER ASSISTED DOMAIN SPECIFIC ENTITY MAPPING METHOD AND SYSTEM," which is hereby incorporated by reference in its entirety. For example, in this specific implementation the various anatomical features 402, 404, 406, 408 represent various axes while the disease severity deviation maps 410, 412, 414, 416 discussed below represent different labels associated with each axis, and so forth.

For each anatomical feature, a number of deviation maps having variations in the extent, or severity level, of a disease or a condition are provided. For example, for anatomical feature "A" 402, a number of reference deviation maps 410 having variations in the extent of a disease or a condition associated with anatomical feature "A" are provided. Similarly, sets of reference deviation maps 412, 414, and 416 are provided, which exhibit the variations in the extent of a disease or condition for each of the remaining respective anatomical features through the Nth feature. As will be appreciated by those of ordinary skill in the art, each of the disease severity reference deviation maps within the respective map sets 410, 412, 414, 416 are generated for the respective anatomical feature 402, 404, 406, 408 and, in the case of image data (rather than non-image data) reference deviation maps, may be further categorized by a tracer or tracers (if one was employed) and by the imaging technology employed. For example, reference deviation maps within the respective deviation map sets 410, 412, 414, 416 may be generated by magnetic resonance (MR) imaging, positron emission tomography (PET), computed tomography (CT), single photon emission-computed tomography (SPECT), ultrasound, optical imaging, or other conventional imaging techniques and by using suitable tracers in appropriate circumstances. As discussed above, the reference deviation maps may also or instead be generated from non-image data, including clinical data.

For each anatomical feature, the disease severity reference deviation maps 410, 412, 414, 416 of the anatomical features are ordered, as generally indicated by arrow 418, according to the severity of the disease or condition or otherwise associated with a severity of the disease or condition. For example, for anatomical feature "A" 402, the disease severity reference deviation maps 410 may be ordered in ascending order from the least extent or amount of the disease or condition, to the highest amount or extent of the disease or condition.

In the depicted embodiment, eight reference deviation maps are depicted in each of disease severity deviation map groups 410, 412, 414, 416 as representing the various disease severity levels associated with each anatomical feature 402, 404, 406, 408. As will be appreciated by those of ordinary skill in the art, however, the number of reference deviation maps in the sets of disease severity deviation maps 410, 412, 414, 416 is arbitrary and can be increased or decreased depending on the implementation and the characteristics of the reviewer. For example, in exemplary embodiments where the comparison process is automated, the number of reference deviation maps within each of the groups of disease severity deviation maps 410, 412, 414, 416 may contain more than eight maps, such as ten, twenty, one hundred, and so forth. Further, though a single disease severity reference deviation map is presently depicted as corresponding to each ordered severity level for each anatomical feature, each degree of severity for each anatomical feature may actually have one or more than one disease severity reference deviation map provided for comparison. For example, in exemplary implementations where the comparison process is automated, each severity level or severity index for an anatomical feature 402, 404, 406, 408 may be represented by more than one disease severity reference deviation map.

Various patient deviation maps 420 may then be evaluated relative to the respective disease severity reference deviation maps 410, 412, 414, 416 to determine an extent of disease or condition in the patient deviation maps 420 in comparison to the respective disease severity reference deviation maps. Each patient deviation map 420 for an anatomical feature may be generated by comparing acquired patient data to normative standardized anatomical data for the respective anatomical feature. As will be appreciated by those of ordinary skill in the art, the patient deviation maps 420 may be derived from images acquired using one or more suitable tracers (e.g., when needed to capture desired functional information), from images acquired through other techniques, or from non-image data, as described above. Therefore, in an exemplary embodiment, the patient deviation maps 420 based on image data are not only compared to a set of disease severity reference deviation maps 410, 412, 414, 416 corresponding to the same anatomical feature 402, 404, 406, 408, but also to those reference maps in the set of disease severity reference deviation maps 410, 412, 414, 416 generated from image data acquired using the same or a comparable tracer or tracers, if present, and using the same or a comparable imaging technology. In an exemplary embodiment, the comparison between the one or more maps of patient deviation maps 420 and the respective set of disease severity reference deviation maps 410, 412, 414, 416 is performed automatically, such as by pattern matching or other suitable comparison techniques and routines.

For example, in one implementation patient deviation maps 420 generated from image data corresponding to the anatomical feature "A" 402 may be automatically compared to the corresponding set of ordered disease severity reference deviation maps 410 that were generated from data acquired using the same tracer or tracers, if a tracer was employed, and using the same imaging modality, such as MR or PET. As will be appreciated by those of ordinary skill in the art, patient deviation maps 420 and the respective disease severity reference deviation maps 410, 412, 414, 416 to which they are compared may vary depending on patient specific factors (such as patient history, patient symptoms, and so forth) as well as clinical factors (such as standard practice for the attending physician and for the medical facility, preliminary diagnoses, years of practice, and so forth).

In the presently illustrated example, each comparison generates a severity index 422 that expresses or represents the extent of disease in the respective patient deviation map 420, as determined by comparison to the anatomical feature-specific disease severity reference deviation maps 410, 412, 414, 416. As will be appreciated by those of skill in the art, in those embodiments in which the comparison is performed automatically, the severity index 422 may also be generated automatically. In such embodiments, a reviewer or evaluator may simply be provided with a severity index 422 for each anatomical feature of interest or for which patient deviation maps 420 were generated or processed.

In some embodiments, an aggregate patient severity score 424 is generated from the severity indices 422 using statistical analysis 426, such as a rules-based aggregation method or technique. In an exemplary embodiment, the aggregate severity score 424 is generated automatically, such as by automatic implementation of the analysis 426 using suitable routines or computer-implemented code. In such embodiments, a reviewer or evaluator may simply be provided with an overall or aggregate severity score for the patient.

Figure 19:
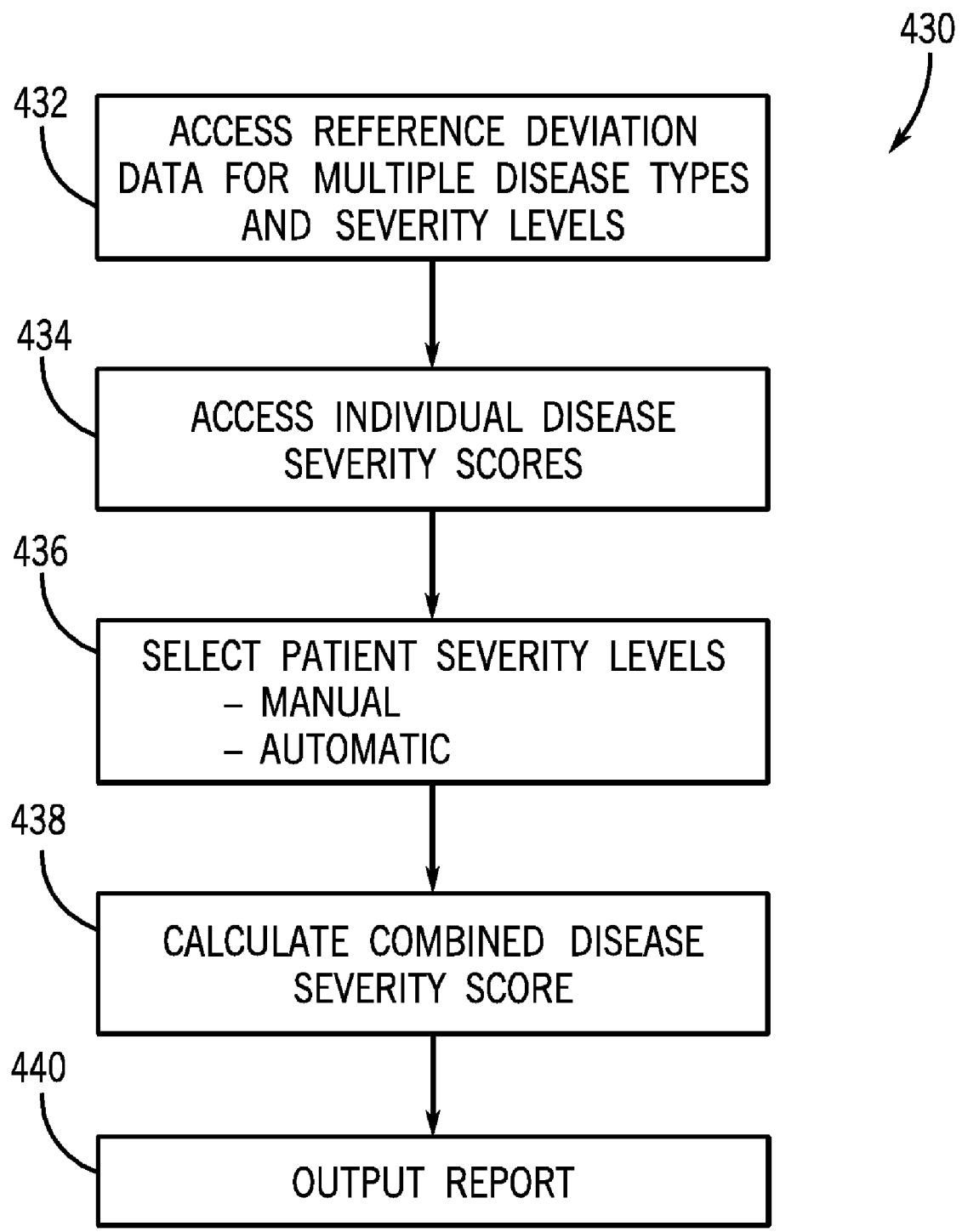
FIG. 19 is a flow chart of an exemplary method for calculating a combined disease severity score in accordance with one embodiment of the present invention.

In addition to calculating disease severity scores or indices for a patient with respect to a single disease type, the presently disclosed data processing system may also calculate a combined disease severity score based on a plurality of different disease types and severity levels. For instance, an exemplary method 430 for determining a combined disease severity score for a patient based on multiple disease types and severity levels is depicted in FIG. 19 in accordance with one embodiment of the present invention. The method 430 may include a step 432 of accessing reference deviation data (such as reference deviation maps or other data) for multiple disease types. Such reference deviation maps may be standardized according to a demographic (or other) characteristic. Additionally, the step 432 may also include accessing reference deviation maps or data with respect to a plurality of severity levels for one or more of the disease types. In one embodiment, the reference deviation data may include functional or structural deviation maps indicative of differences between normal individuals and individuals diagnosed with particular disease types, or diagnosed with severity levels of the different disease types. Disease severity scores may be associated with subsets of the reference deviation data, such as the different reference deviation maps associated with various severity levels, as generally discussed above. These individual disease severity scores may also be accessed in a step 434.

The method 430 may also include selecting patient disease severity levels in a step 436. Selection of patient disease severity levels may be performed in a variety of manners. In one embodiment, a user may compare a patient deviation map to a library or database of known deviation maps indicative of functional or structural deviation associated with various disease types and/or severity levels. An exemplary visual reference library 484 of known, standardized deviation maps corresponding to normal patients and patients diagnosed with various disease types, is generally illustrated in, and discussed in greater detail below with respect to, FIGS. 21 and 22. In such an embodiment, the user may compare a patient deviation map to those reference deviation maps included in the library 484 to diagnose the patient as having one or both of a particular disease type and severity level. To facilitate such manual analysis and comparison, in one embodiment, one or more of the reference deviation maps or patient deviation maps may be displayed by a computing system, and a user may indicate (via a user-interface) a selection of a particular severity level for each disease type corresponding to the reference deviation map closest to the patient deviation map.

In another embodiment, a computing system, such as the data processing system 34, may be programmed to automatically compare the patient deviation map to reference deviation maps in the library of reference deviation maps and to automatically select the closest matches. Alternatively, various disease scores may be calculated based on given diseases and severity levels and compared to a patient disease score to automatically determine and select the closest match. In yet another embodiment, a computing system may apply an algorithm to select a subset of the reference deviation maps, from which a user may make the final selections.

Following selection of patient severity levels for a plurality of disease types, a combined disease severity score may be automatically calculated in step 438. Finally, a report including or based on the combined disease severity score may be output in a step 440. As generally noted above, outputting of the report, as well as other reports and data described herein, may include outputting the report to memory, outputting the report to a user, or outputting the report to a different software routine for further processing.

Figure 20:
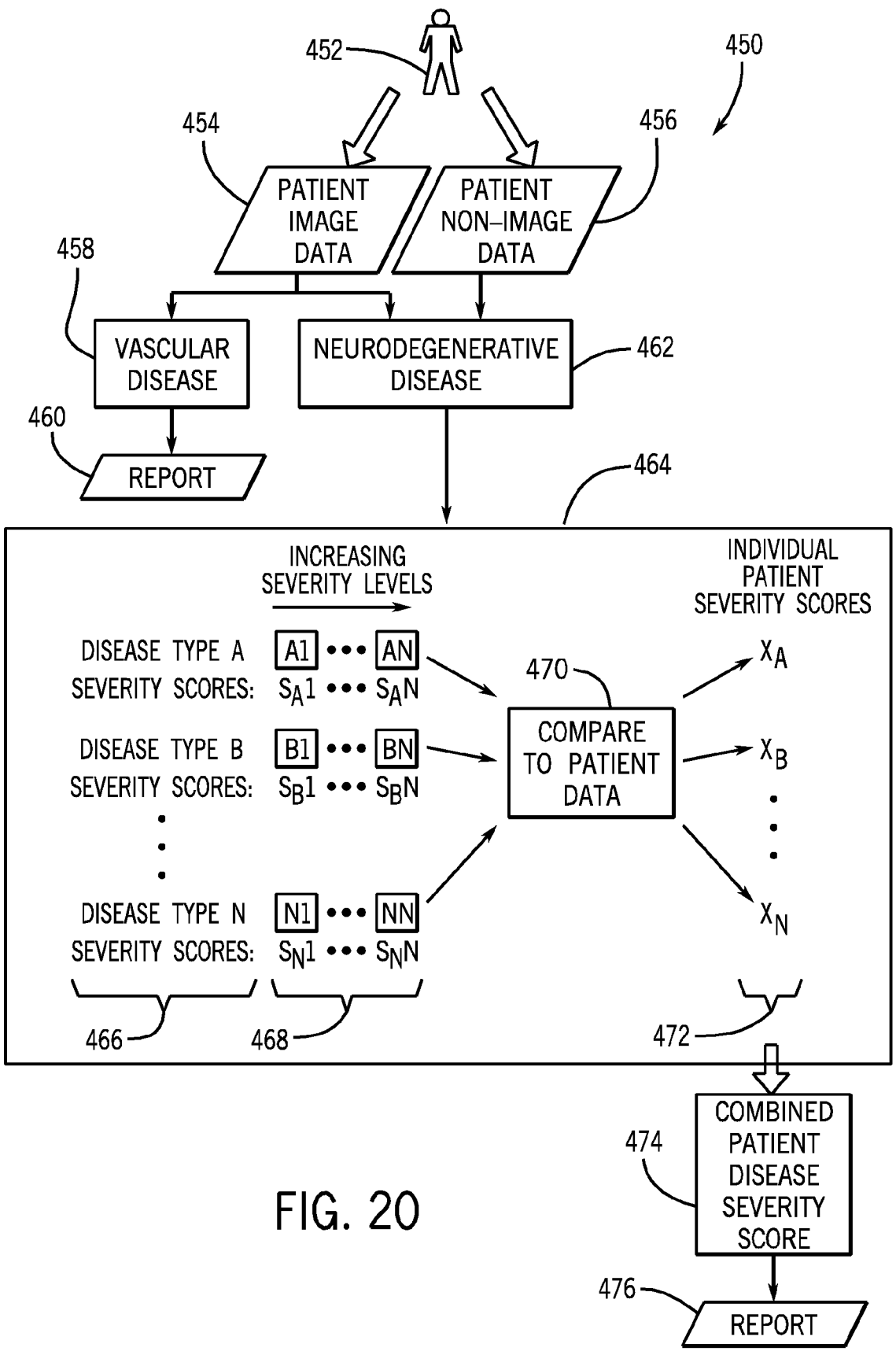
FIG. 20 is a block diagram generally illustrating a process for comparing patient data to standardized data for a plurality of disease types and severity levels in accordance with one embodiment of the present invention.

The method 430 described above may be employed in connection with a variety of anatomical regions and disease types, including, but not limited to, brain disorders. An exemplary process for evaluating such brain disorders may be better understood with reference to block diagram 450, which is illustrated in FIG. 20 in accordance with one embodiment of the present invention. Patient image data 454 and patient non-image data 456 may be collected from a patient 452. As noted elsewhere herein, such patient image data may include images obtained through any of various imaging modalities, and may include patient cortical thickness maps, patient cortical thickness deviation maps or any other desired image data. As also previously discussed, the patient non-image data 456 may include numerous data types and information, such as results of clinical tests and laboratory tests, family history, genetic history, and so forth. Based on the patient image data 454, it may be determined that the patient 452 has a vascular disease, as generally indicated in block 458. Such a determination or diagnosis may be output in a report 460. The patient image data 454 and the patient non-image data 456 may also be used to determine whether the patient 452 has a neurodegenerative disease, as generally indicated in block 462.

Block 464 generally represents a work flow for determining patient severity levels for a plurality of brain disorders or disease types 466. Separate pluralities of reference deviation maps 468 may be associated with each disease type, and each plurality may generally represent different severity levels of its respective disease type. Further, each reference deviation map may be associated with a disease severity score (e.g., of the series S1 ... SN for each disease type). For example, in one embodiment, the reference deviation map representative of the lowest severity level of a particular disease may be associated with the lowest disease severity score (i.e., S1) for that disease type, while other reference deviation maps indicative of increasing severity levels of the disease type may be associated with increasing disease severity scores (i.e., S2, S3, . . . , SN). Either or both of patient image data 454 and patient non-image data 456 may be compared (block 470) to the sequence of reference deviation maps for disease type A to determine a patient severity level 472 for disease type A. The individual patient severity score $X_A$ for disease type A may equal the disease severity score associated with the reference deviation map for disease type A closest to the patient data to which it is compared. Alternatively, if the patient data suggests that the patient severity falls somewhere between two of the reference deviation maps for disease type A, the individual patient severity score $X_A$ may be computed from the two disease severity scores associated with the individual reference deviation maps closest to the patient data. The individual severity scores for other disease types may be calculated in a similar manner based on their own associated reference deviation maps.

Once the individual patient severity scores 472 for each disease type is calculated, such individual scores may be utilized to calculate a combined patient disease severity score, as generally shown in block 474. The combined patient disease severity score may be calculated through addition of the individual patient severity scores, averaging of the individual patient severity scores (which may be weighted as desired), or in any other suitable fashion. Further, the combined patient disease severity score may also indicate the relative contribution of each disease type to a patient condition. For instance, the combined patient disease severity score may indicate that Alzheimer's disease is the primary contributing factor to patient dementia or some other condition. In another embodiment, the combined patient disease severity score may indicate the relative contribution of each of a plurality of disease types to a patient condition. By way of example, the combined patient disease severity score may indicate the relative contribution of various brain disorders to patient dementia (e.g., 40% AD, 30% FTD, 30% other). A report 476 based on or indicative of the combined patient disease severity score may be output to a user or to storage.

As noted above, reference images and deviation maps of an exemplary visual reference library 484 are depicted in FIGS. 21 and 22 in accordance with one embodiment of the present invention. It is noted that the presently depicted representations are merely provided for illustrative purposes, and that an actual implementation of a visual reference library may include different or additional images. Indeed, various embodiments of a visual reference library 484 may include a significantly greater number of images, such as tens, hundreds, or even greater numbers of reference images or maps, which may be standardized in various embodiments as discussed above. It will be further appreciated that images within the visual reference library 484 may be obtained via one or any number of imaging modalities, and may include original images, deviation maps such as those discussed above, or any other suitable reference images. In the presently illustrated embodiment, the reference images generally denote metabolic rate deviations between normal individuals and individuals diagnosed with various brain disorders. In other embodiments, however, other deviation maps, such as cortical thickness deviation maps, cerebral blood flow rate deviation maps, or even deviation maps for non-brain anatomies, may be included in the visual reference library 484.

In the presently illustrated embodiment, the visual reference library 484 is depicted as including a set of reference images 486 for normal persons, and reference deviation maps 488 and 490 corresponding to patients clinically diagnosed with mild and severe forms, respectively, of Alzheimer's disease (AD). The visual reference library 484 may also include deviation maps 492 corresponding to patients diagnosed with diffuse cortical Lewy body disease (DLBD) and deviation maps 494 representative of patients clinically diagnosed with frontotemporal dementia (FTD). The visual reference library 484 may also include additional deviation maps, such as maps 496 associated with progressive supranuclear palsy (PSP), maps 498 associated with multi-infarct dementia (MID), and maps 500 associated with normal pressure hydrocephalus (NPH).

Technical effects of one or more embodiments of the present invention may include the diagnosis of various patient disease types and severity levels, as well as providing decision support tools for user-diagnosis of patients. In one embodiment, technical effects include the visualization of patient clinical image and non-image information together in a holistic, intuitive, and uniform manner, facilitating efficient diagnosis by an observer. In another embodiment, technical effects include the calculation of patient cortical deviation maps and reference cortical deviation maps of known brain disorders, the calculation of additional patient and reference deviation maps, and the combination of such maps with other clinical tests, to enable quantitative assessment and diagnosis of brain disorders.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method comprising:
   accessing an image deviation score of a patient derived through a comparison of patient image data to standardized image data representative of a population of individuals;
   accessing a non-image deviation score of a patient derived through a comparison of patient non-image data to standardized non-image data representative of the population of individuals;
   processing the image deviation score and the non-image deviation score to generate a visual output indicative of both a difference between the patient image data and the standardized image data, and a difference between the patient non-image data and the standardized non-image data; and
   displaying the visual output to facilitate diagnosis of a medical condition of the patient.

2. The method of claim 1, wherein accessing the image deviation score includes calculating the image deviation score.

3. The method of claim 2, wherein calculating the image deviation score includes calculating the image deviation score based on at least one of projection deviation, single pixel deviation, or single voxel deviation of the patient image data from the standardized image data.

4. The method of claim 1, wherein the image deviation score includes at least one score based on deviation of the patient image data from the standardized image data with respect to at least one of metabolic activity of the brain of the patient, physical anatomy of the brain, or functional activity of the brain.

5. The method of claim 1, wherein the patient image data includes image data obtained from the patient via at least two imaging systems of different modalities.

6. The method of claim 5, wherein the at least two imaging systems include at least two of the following: a computed tomography imaging system, a magnetic resonance imaging system, a positron emission tomography imaging system, a single photon emission computed tomography imaging system, or a digital tomosynthesis imaging system.

7. The method of claim 1, wherein the population of individuals includes individuals sharing a substantially common characteristic with the patient, and wherein at least one of the standardized image data or the standardized non-image data is standardized based on the substantially common characteristic such that the accessed image or non-image deviation score is indicative of a deviation of the patient image data or patient non-image data from the respective standardized image or non-image data representative of the individuals sharing the substantially common characteristic with the patient.

8. The method of claim 7, wherein the substantially common characteristic includes at least one of age, race, or gender.

9. The method of claim 7, wherein the standardized image data includes averaged image data for the individuals sharing the substantially common characteristic.

10. The method of claim 1, wherein accessing the non-image deviation score includes calculating the non-image deviation score.

11. The method of claim 1, wherein the patient non-image data includes patient clinical data.

12. The method of claim 1, wherein the patient non-image data includes patient data regarding one or more of the following: patient history, patient vital signs, functional tests, cognitive tests, neurological tests, or genetic tests.

13. The method of claim 1, wherein the visual output includes a graphical representation that emphasizes the magnitude of the difference between the patient image or non-image data and the respective standardized image or non-image data.

\* \* \* \* \*